United States Patent [19]
Tanihara et al.

[11] Patent Number: 5,658,592
[45] Date of Patent: Aug. 19, 1997

[54] MEDICAL CROSSLINKED POLYMER GEL OF CARBOXYLIC POLYSACCHARIDE AND DIAMINOALKANE

[75] Inventors: Masao Tanihara, Kurashiki; Hisao Kinoshita, Ikoma, both of Japan

[73] Assignee: Kuraray Co., Ltd., Kurashiki, Japan

[21] Appl. No.: 571,976
[22] PCT Filed: May 8, 1995
[86] PCT No.: PCT/JP95/00873
 § 371 Date: Jan. 16, 1996
 § 102(e) Date: Jan. 16, 1996
[87] PCT Pub. No.: WO95/31223
 PCT Pub. Date: Nov. 23, 1995

[30] Foreign Application Priority Data

May 13, 1994 [JP] Japan .................................. 6-124158

[51] Int. Cl.⁶ .................................................. A61K 9/10
[52] U.S. Cl. ...................... 424/488; 514/944; 252/315.3; 252/315.4
[58] Field of Search .................... 424/486, 488; 514/944; 252/315.3, 315.4

[56] References Cited

U.S. PATENT DOCUMENTS 4,452,892  6/1984  Rosevear .................................. 435/176

Primary Examiner—Edward J. Webman
Attorney, Agent, or Firm—Oblon, Spivak, McClelland, Maier & Neustadt, P.C.

[57] ABSTRACT

A water swelling polymer gel produced by covalently crosslinking a polysaccharide having a carboxyl group within the molecule with a diaminoalkane derivative as the crosslinking reagent. The medical polymer gel is useful as the structural component of wound dressings, adhesives for biological tissues, adhesion preventing agents, bone reinforcing agents, and drug releasing base materials. Wound dressings comprising the structural material of the water swelling polymer gel of the present invention, can be applied to a patient with wound, burn, and decubitus to promote the healing of the wounds of the patient.

5 Claims, 3 Drawing Sheets

5,658,592

MEDICAL CROSSLINKED POLYMER GEL OF CARBOXYLIC POLYSACCHARIDE AND DIAMINOALKANE

TECHNICAL FIELD

This is a National Stage Application of PCT/JP95/00873 filed May 8, 1995.

The present invention relates to a medical polymer gel. More specifically, the present invention relates to a novel medical polymer gel having a drug releasing property. The medical polymer gel of the present invention is useful as the structural component for wound dressings, adhesives for biological tissues, adhesion preventing agents, bone reinforcing materials, and drug releasing base materials.

The present invention also relates to a novel water swelling polymer gel consisting of polysaccharide having excellent transparency, thermal resistance, biocompatibility and stability. The water swelling polymer gel provided by the present invention is useful as the structural component of medical polymer gels and also useful as the structural component of medical materials such as wound dressings, adhesion preventing agents and adhesives for biological tissues because the polymer gel itself has excellent thermal resistance and biocompatibility. Furthermore, because the polymer gel has excellent transparency, the polymer gel is useful as the structural component of wound dressings and adhesion preventing agents, in particular.

BACKGROUND ART

In the present specification, the term "water swelling polymer gel" means a polymer gel, being capable of swelling in body fluids such as blood, plasma and intercellular fluid or fluids similar to body fluids, and having biocompatibility. As such water swelling polymer gel consisting of polysaccharide, it is known a gel composed of agar, agarose and carrageenan. Chemically crosslinked dextran or cellulose gel, calcium-ion crosslinked alginate gel, and a gel composed of chitin or chitosan are also known.

The application of water swelling polymer gels to medical practice is exemplarily found in wound dressings, contact lens, intraocular lens, adhesives for biological tissues, adhesion preventing materials, adsorbents for blood purification, hybrid artificial organs such as artificial pancreas and artificial liver, artificial cartilage, base materials for releasing drugs in a sustained manner and the like. Because water swelling polymer gels have compositions and mechanical properties similar to those of biological tissues, such gels may be applied in a wide variety of fields in the future.

Gauze and ointments have been used conventionally for treating wounds such as injury and burn, ulcer, and decubitus. These have effects of absorbing exudates and preventing the penetration of exogenous bacteria and the like. It has been indicated recently that a variety of growth factors (bFGF, TGFβ, etc.) promoting wound healing are present in the exudates from the wounds (see Howell, J. M., Current and Future Trends in Wound Healing, Emerg. Med. Clin. North Amer., 10, 655–663 (1992)). Therefore, attention has been focused on an occlusive dressing having the effect of promoting wound healing while holding the growth factor on the wound (Eaglstein, W. E., Experience with biosynthetic dressings, J. Am. Acad. Dermatol., 12, 434–440 (1985)).

As the occlusive dressings, use may be made of polyurethane film, hydrocolloid, non-woven fabric of alginate fiber, polyvinyl alcohol sponge, and water swelling polymer gels comprising polyethylene glycol and polyacrylamide.

As such adhesive for biological tissues, use may be made of cyanoacrylate polymerizable adhesives, fibrin glue and the like.

As adhesion preventing agents, those composed of oxycellulose mesh are known.

As the method for producing these water swelling polymer gels, it is known a method of producing solid matters of amylose, dextran or pullulan, crosslinked with succinate or glutarate (see the Specification of U.S. Pat. No. 4,002,173). These are preferable as a hemostatic agent. Also, it is known crosslinked chitosan produced by reacting chitosan with N-hydroxysuccinimide ester (see Japanese Patent Laid-open No. Hei 2-180903). This is useful in the field relating to medicines, such as artificial skins. Furthermore, viscous and elastic fluid is also produced by ionically crosslinking temporarily a chitin derivative with sulfuric acid, aspartic acid, glutamic acid and the like, and is used for preventing adhesion (see the Specification of U.S. Pat. No. 5,093,319).

As the essential property, however, biocompatibility should be demanded for the medical material in addition to the usefulness for medical purpose. A great number of medical materials have been developed conventionally, but it has not yet been known any material with biocompatibility, which can satisfy all of various medical use. Attempts have been made of the application of water swelling polymer gels consisting of polysaccharide having the composition and mechanical properties similar to those of living bodies to medical purpose, but because the stability and strength of the gels are low, few of them can be resistant to steam sterilization. Thus, the gels are problematic as medical devices.

Sterilization essential for the production of medical devices includes formalin sterilization, ethylene oxide gas sterilization, steam sterilization, or radiation sterilization. In the formalin sterilization and ethylene oxide gas sterilization of water swelling polymer gels, complete removal of residual drugs is hard, involving possible residual toxicity. Steam sterilization is a highly safe sterilization process with no residual matters, and the apparatus therefor is not expensive. However, few water swelling polymer gels can resist the severe sterilization conditions of 121° C. for 20 minutes. Radiation sterilization is a highly safe sterilization method with no residual matters, but the method is problematic because the irradiation systems are expensive and the properties of water swelling polymer gels may be modified due to radiation generated radicals from water, which may cleave chemical bonds and induce crosslinking reactions.

Additionally, gels of agar, agarose, carrageenan and the like are not suitable as the structural component of medical devices because the gels with a lower mechanical strength dissolve under heating. Gels of crosslinked dextran or cellulose do not dissolve under heating, but the gels may turn rigid by a crosslinking process and acquires a low water content, involving poor biocompatibility. Furthermore, the gels may be colored or may be opaque through crosslinking. Calcium ion-crosslinked alginate gel with a higher crosslinking degree may be semi-opaque or the gel may gradually dissolve in body fluid or in physiological salt solutions during ion exchange, problematically. Also, the gel has a lower mechanical strength so that the gel is readily broken. It is also problematic that chitin and chitosan dissolve in body fluid or they may be solubilized via bacterial infection.

Polyurethane film to be used as wound dressings is not water absorbable although the film has higher transparency and occlusive potential, so the film cannot be used for the wounds with much exudates. Non-woven fabric composed of alginate fiber hydrocolloid, polyvinyl alcohol sponge and the like, all have retentivity of exudates. Because they are opaque, however, wounds cannot be observed. Furthermore, hydrocolloid dressings do not have bioabsorbability, and therefore, the principal components thereof remain in biological tissues for a long term, inducing chronic inflammation, disadvantageously (see Young, S. R. et. al., J. Invest. Comparison of the effect of semi-occlusive polyurethane dressings and hydrocolloid dressings on dermal repair: 1. Cellular changes. Dermatol., 97, 586–592 (1991)). Some of the water swelling polymer gels composed of polyethylene glycol and polyacrylamide have good transparency, but without bioabsorbability because the gels are synthetic polymers. Hence, the gels remain in wounds as in the case of hydrocolloid dressings, possibly inducing chronic inflammation. The two monomers thereof as the raw materials have higher toxicity, with possible development of toxicity due to the remaining monomers and decomposed products thereof.

Also, occlusive dressings such as polyurethane film and hydrocolloid are excellent in terms of the effect of facilitating healing. Once the dressings are infected with bacteria, however, the bacteria rapidly proliferate because the wet environment is a suitable medium for the bacteria, with a risk of triggering severe infection. For the infection, antibiotics are administered systemically or locally, but blood circulation is so poor at wounds with bacterial infection that an effective dose of antibiotics cannot be delivered to the wounds by the systemic administration, or side effects may occur by local administration due to the cytotoxicity of locally administered antibiotics.

Cyanoacrylate polymerizable adhesives to be used for biological tissues have problems in that the monomer is highly cytotoxic; fibrin glue has also problems in that the stable supply and the retention of the properties thereof are difficult because the glue is derived from living bodies and the glue may possibly be infected with virus.

Oxycellulose mesh to be used as an adhesion preventing agent is poor in handling because the mesh is in the form of fabric. Additionally, the mesh has poor biocompatibility. Therefore, such mesh is disadvantageous in that chronic inflammation might be induced.

Succinate or glutarate crosslinked amylose, dextran or pullulan, which can be produced by a production method disclosed in the Specification of U.S. Pat. No. 4,002,173, is preferable as a hemostatic agent. However, because such amylose, dextran or pullulan is in the form of solid matters, it lacks flexibility. As described in the Specification, it is essential that the solid matters should be modified into ground powder or sponge. Thus, the aforementioned amylose, dextran or pullulan cannot satisfy the transparency and occlusive potential demanded for wound dressings and adhesion preventing materials. Furthermore, the ester bond used for such crosslinking is readily hydrolyzed in an aqueous solution or in body fluid, and therefore, the properties as a water swelling gel are deteriorated over time. Additionally, solubilized matters increase, which is a problem from safety concern. In practical sense, these are for the purpose of the practical application as a hemostatic agent for a short term of several hours. Therefore, these can never endure the continuous use for several days to several months.

It is known crosslinked chitosan produced by reacting chitosan with an N-hydroxysuccinimide ester compound (see Japanese Patent Laid-open No. Hei 2-180903), and it is expected that the chitosan may be useful in the medical fields such as artificial skin. According to the Example, the crosslinked chitosan is rigid and therefore fragile with a breaking extension ratio of 30% or less, so that the chitosan cannot satisfy the elasticity and flexibility demanded for wound dressings and adhesion preventing materials. The chitosan is hydrolyzed in aqueous solution or body fluid because of the ester bonds present therein, generating solubilized matters and deteriorating the properties of the water swelling polymer gel.

It is known also a method of preventing tissue adhesion using a viscous and elastic fluid produced by ionically crosslinking temporarily a chitin derivative with sulfuric acid or aspartic acid or glutamic acid (see the Specification of U.S. Pat. No. 5,093,319), but because the crosslinking is via a reverse ion bonding, the properties of the resulting water swelling polymer gel are deteriorated in contact with a solution containing a higher concentration of salts, such as body fluid.

As has been described above, no water swelling polymer gel with all of the properties required for various medical use and concurrently with biocompatibility is found among conventionally known such gels in the current state.

Alternatively, polymer gels have been used in various applications in medical fields as described above. It has been proposed recently a drug delivery system (DDS) containing a pharmaceutical agent in a polymer gel or a wound dressing containing a pharmaceutical agent.

The examples are a crosslinked hyaluronate gel containing lipid microspheres with pharmaceutical agents encapsulated therein and being cleavable with OH radicals (see Yui, et al., Polymer Preprints, Japan, 42(8), pp. 3186–3188 (1993)); and cellulose powder bound, through -Phe-, -Tyr-, -Ile-Tyr- and -Gly-Ile-Tyr-, with pholcodine (see F. Lapicque & E. Dellacherie, J. Controlled Release, 4, pp. 39–45 (1983)). As wound dressings with pharmaceutical agents contained therein, it is known a wound contact pad as a part of a wound treating device, comprising a mixture alginate of an insoluble alginate salt and a soluble alginate salt, and containing an antibiotics or a local anesthesia (see the Specification of U.S. Pat. No. 5,238,685). It is also described a wound dressing containing hydrogel, as the structural component, in which a peptide promoting healing of wounds is covalently bonded at least at the surface and also containing, a disinfectant (see WO 92/3172).

By the drug delivery system in which drug encapsulated-lipid microspheres is contained in a crosslinked hyaluronate gel to be decomposed via OH radicals, the hyaluronate gel is decomposed at a site where OH radicals are generated to release the drug encapsulated-lipid microspheres. Because the generation of higher levels of OH radicals is limited to a certain stage of inflammation or to a very limited area of inflammation, however, the number of subjective diseases to which the system is applicable is relatively limited. Additionally, applicable drugs are substantially limited because drugs with lower fat solubility cannot be encapsulated into lipid microspheres. Furthermore, the drugs encapsulated into lipid microspheres are gradually released from the lipid microspheres into an external aqueous phase so that the drugs may be released also at a site besides the focal site, involving possible side effects. By a drug delivery system in which pholcodine is bound through -Phe-, -Tyr-, -Ile-Tyr-, and -Gly-Ile-Tyr- to cellulose powder, the drug immobilized onto the cellulose powder is tentatively released in the presence of an enzyme, but the release of the drug is as less as 1/1000 to 1/20,000 fold that of the immobilized drug. Thus, such system is not practical.

In the wound dressings disclosed in U.S. Pat. No. 5,238,685, drugs such as antibacterial agents and local anesthesia may be contained in a gel pad, but the drugs are consistently released because the drugs are not immobilized onto the gel, thus possibly inducing side effects. In the wound dressing disclosed in WO 92/3172, the surface thereof is chemically bound with a peptide for promoting wound healing and the bonding cannot be cleaved. Thus, the effect of the peptide can be exerted only at a site in contact to the wound dressing. If a disinfectant is contained in the structural component hydrogel, the disinfectant is consistently released, with concerns of the occurrence of side effects.

As has been described above, no conventionally known medical polymer gel can release a therapeutically effective dose of a drug only at a subjective focal site. Hence, a safer therapeutic system is now desired.

Thus, a first objective of the present invention is to provide a medical polymer gel capable of releasing a therapeutically effective dose of a drug only at a focal site generating an enzyme.

Furthermore, a second objective of the present invention is to provide a water swelling polymer gel, being highly transparent and having excellent biocompatibility, thermal resistance and stability, and being useful as the structural component of a variety of medical materials such as wound dressings, adhesives for biological tissues, adhesion preventing agents and the like.

DISCLOSURE OF THE INVENTION

The present inventors have carried out various investigations so as to overcome the problems. The present inventors have found that the first objective can be achieved by providing a medical polymer gel wherein a drug is immobilized onto a water swelling polymer gel through a cleavable group with the main (i.e., principal) chain to be cleaved via an enzymatic reaction and a spacer.

Furthermore, the inventors have found that the second objective can be achieved by providing a water swelling polymer gel produced by covalently crosslinking polysaccharides with carboxyl groups contained in the molecule with diaminoalkane or a derivative thereof.

On the basis of these findings, the present invention has been achieved after further investigations.

In summary, the present invention relates to the following:

(1) a medical polymer gel produced by immobilizing a drug, through a cleavable group with the main chain to be cleaved via an enzymatic reaction and a spacer, onto a water swelling polymer gel in a sequence represented by the following general formula (I):

A-B-C-D    (I)

(wherein A represents the water swelling polymer gel; B represents the spacer; C represents the cleavable group with the main chain to be cleaved by the enzymatic reaction; and D represents the drug):

(2) a medical polymer gel described in the item (1), wherein the spacer is a molecular chain with the total number of carbon atoms, nitrogen atoms and oxygen atoms contained in the main chain being above 4:

(3) a medical polymer gel described in the item (1), wherein the cleavable group with the main chain to be cleaved via an enzymatic reaction is selected from the group consisting of -Val-Pro-Arg-, -(Ala)$_2$-Pro-Val-, -Ala-Gly-Phe-, -(Ala)$_3$-, -Asp-Glu-, -(Ala)$_2$-Phe-, -(Ala)$_2$-Pro-Phe-, -Gly-Phe-Leu-Gly-, -(Arg)$_2$-, and -Phe-Arg-:

(4) a medical polymer gel described in any one of the items (1) to (3), wherein the water swelling polymer gel is a water swelling polymer gel produced by covalently crosslinking a polysaccharide having a carboxyl group within the molecule with a crosslinking reagent represented by the following general formula (II)

R$^1$HN—(CH$_2$)$_n$—NHR$^2$    (II)

(wherein n represents an integer of 2 to 18; and R$^1$ and R$^2$ independently represent hydrogen atom or the group represented by —COCH(NH$_2$)—(CH$_2$)$_4$—NH$_2$) or a salt thereof:, (5) a medical polymer gel described in the item (4), wherein the polysaccharide having a carboxyl group within the molecule is a salt of alginic acid or a salt of hyaluronic acid:

(6) a medical polymer gel described in the item (4), wherein the salt of the crosslinking reagent is the N-hydroxysuccinimide salt:

(7) a medical polymer gel described in the item (6), wherein the N-hydroxysuccinimide salt of the crosslinking reagent is selected from the group consisting of 2N-hydroxysuccinimide salt of diaminoethane, 2N-hydroxysuccinimide salt of diaminohexane, 4N-hydroxysuccinimide salt of N,N'-di(lysyl)-diaminoethane, and 3N-hydroxysuccinimide salt of N-(lysyl)-diaminohexane:

(8) a water swelling polymer gel produced by covalently crosslinking a polysaccharide having a carboxyl group within the molecule with a crosslinking reagent represented by the following general formula (II)

R$^1$HN—(CH$_2$)$_n$—NHR$^2$    (II)

(wherein n represents an integer of 2 to 18; and R$^1$ and R$^2$ independently represent hydrogen atom or the group represented by —COCH(NH$_2$)—(CH$_2$)$_4$—NH$_2$) or a salt thereof:

(9) a water swelling polymer gel described in the item (8), wherein the polysaccharide having a carboxyl group within the molecule is a salt of alginic acid or a salt of hyaluronic acid:

(10) a water welling polymer gel described in the item (8) or (9), wherein the salt of the crosslinking reagent is the N-hydroxysuccinimide salt: and

(11) a water swelling polymer gel described in the item (10), wherein the N-hydroxysuccinimide salt of the crosslinking reagent is selected from the group consisting of 2N-hydroxysuccinimide salt of diaminoethane, 2N-hydroxysuccinimide salt of diaminohexane, 4N-hydroxysuccinimide salt of N,N'-di(lysyl)-diaminoethane, and 3N-hydroxysuccinimide salt of N-(lysyl)-diaminohexane.

BEST EMBODIMENTS FOR CARRYING OUT THE INVENTION

Figure 1:
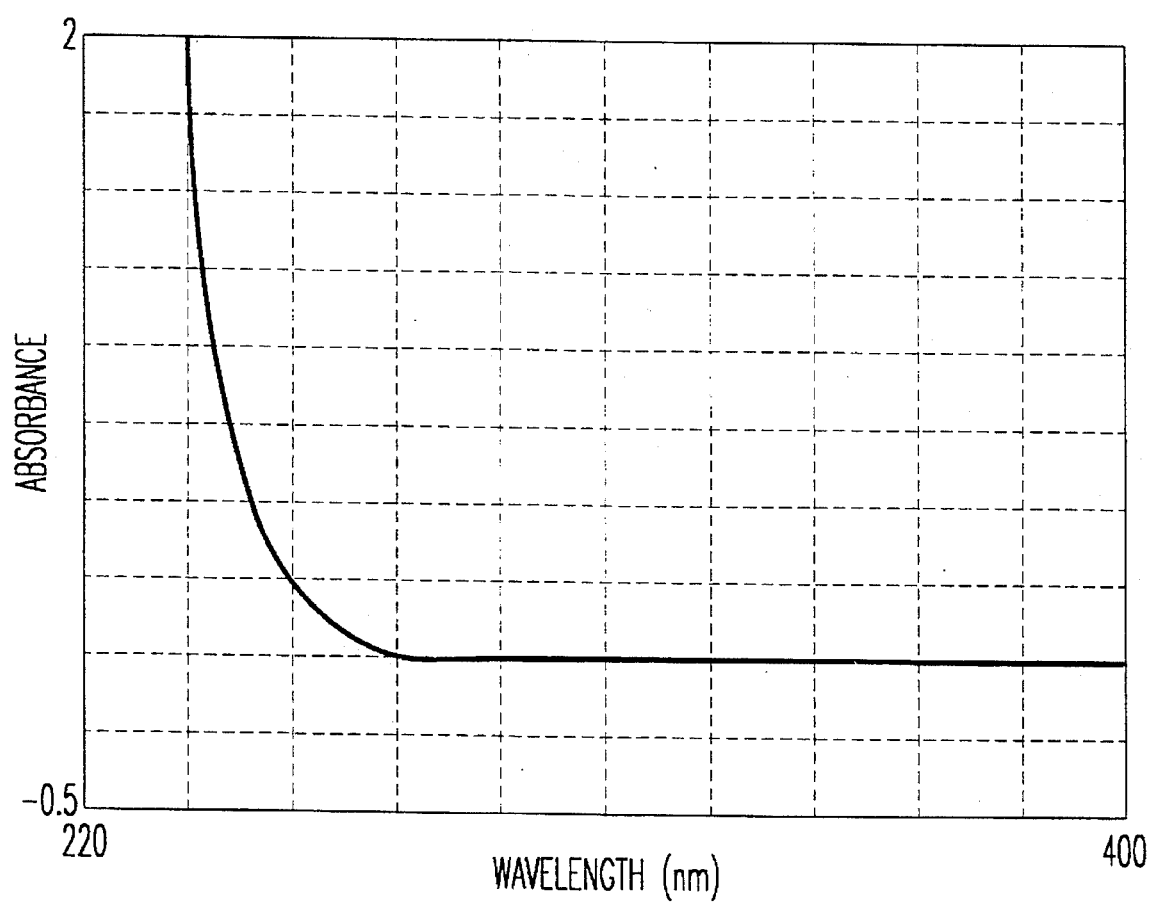
FIG. 1 depicts the UV absorption spectrum chart at 220 nm to 400 nm of the Algin-EDA-Gly of Example 8 in an aqueous 0.05M NaHCO$_3$ solution, analyzed by a Beckman spectrometer Type DU-65 using a photo-cell of a 1-cm optical path for measuring absorbance.

The medical polymer gel in accordance with the present invention is produced by immobilizing a drug, through a cleavable group with the main chain to be cleaved via an enzymatic reaction and a spacer, onto a water swelling polymer gel in a sequence represented by the following general formula (I):

A-B-C-D  (I)

In the formula, A represents the water swelling polymer gel; B represents the spacer; C represents the cleavable group with the main chain to be cleaved by the enzymatic reaction; and D represents the drug.

The water swelling polymer gel A swells in body fluids such as blood, plasma and intercellular fluid or fluids similar to body fluids such as physiological saline, and also have biocompatibility, the type of the water swelling polymer gel is not specifically limited. The polymer material constructing the polymer gel includes, for example, polysaccharides such as alginic acid, chitin, chitosan, hyaluronic acid, cellulose, the derivatives thereof and the like; proteins such as gelatin, collagen, casein, albumin and the like; polypeptides such as polyaspartic acid, polyglutamic acid, polylysine and the like; synthetic polymers such as polyvinyl alcohol (PVA), ethylene vinyl alcohol copolymers, polyvinylpyrrolidone (PVP), polyacrylic acid and the derivatives thereof and the like. By crosslinking a compound from these polymer materials singly or a mixture of two or more of the materials with covalent bonds, hydrophobic bonds, hydrogen bonds, electrostatic bonds and the like, a water swelling polymer gel can be obtained. For example, an electrostatically crosslinked gel can be produced by adding a multivalent metal ion such as $Ca^{++}$ ion to a polymer material with a carboxyl group, such as alginic acid, polyacrylic acid, polyaspartic acid, polyglutamic acid, and a derivative thereof. Similarly, by mixing such polymer material having a carboxyl group into a polymer material with an amino group, such as chitosan, polylysine and the like, an electrostatically crosslinked gel can be produced. By cooling an aqueous solution of gelatin, PVA and a derivative thereof or a solution thereof in an organic solvent, a gel crosslinked via a hydrogen bond can be produced. Provided that a polymer material is ethylene vinyl alcohol copolymer, polyacrylic acid and a derivative thereof, which is dissolved in a water-miscible organic solvent, a solution produced by dissolving the material in a water-miscible organic solvent is immersed in water to generate a gel crosslinked via hydrogen bond and/or hydrophobic bond. In the case of a polymer material with a reactive group such as alginic acid, hyaluronic acid, chitosan, protein, polylysine, polyaspartic acid, polyglutamic acid, polyacrylic acid, PVA and a derivative thereof, a gel crosslinked via covalent bonds can be produced by covalently bonding the polymer material with a multi-functional compound such as lysine oligomer, ethylenediamine, a diaminoalkane derivative, glycerine, succinic acid, oxalic acid and the like. Furthermore, a gel crosslinked via a hydrophobic bond can be produced by bonding such a polymer material as an alkylated oligopeptide, fatty acid, an aliphatic amine, an aliphatic alcohol and a derivative thereof with a hydrophobic compound. During the polymerization of a synthetic polymer material such as polyacrylic acid, PVA, PVP, and a derivative thereof, a multi-functional monomer such as bisacrylamide, ethylene glycol bismethacrylate and the like should be copolymerized with the synthetic polymer material to generate a covalently crosslinked gel. Specifically, preference is given to gels crosslinked via a hydrophobic bond, via an electrostatic bond and via a covalent bond, each gel containing a polysaccharide such as alginic acid as the polymer material; and gels crosslinked via a hydrogen bond and via a hydrophobic bond, each gel containing PVA as the polymer material.

Particularly, preference is given to a water swelling polymer gel (sometimes abbreviated as "water swelling polymer gel (II)" hereinbelow) produced by covalently crosslinking a polysaccharide having a carboxyl group within the molecule with a crosslinking reagent represented by the following general formula (II):

$R^1HN-(CH_2)_n-NHR^2$  (II)

(wherein n represents an integer of 2 to 18; and $R^1$ and $R^2$ independently represent hydrogen atom or the group represented by $-COCH(NH_2)-(CH_2)_4-NH_2)$ or a salt thereof. As will be described hereinafter, the water swelling polymer gel (II) is principally composed of a covalently crosslinked gel, having a higher mechanical strength and being excellent in terms of stability and thermal resistance. Therefore, the gel can be sterilized readily. Additionally, because the gel has greater water retentivity, the gel has greater biocompatibility in particular. Also, the gel is extremely transparent, so that the gel has a great number of advantages such as an easy observation of wound sites without removal of it.

The PVA to be used as the structural material of the polymer material should have an average polymerization degree of 1500 or more and a saponification degree of 60 to 100%. From the respect of the strength of the resulting gel, more preferably, the PVA should have an average polymerization degree of 4,000 or more; most preferably, the PVA should have an average polymerization degree of 10,000 or more. From the respect of the strength of the resulting gel, preferably, the PVA should have a syndiotacticity of 50% or more by Diad expression. More preferably, the PVA should have a syndiotacticity of 53% or more.

The surface of cells and tissues has a hydrogel-like structure containing a greater amount of water due to the presence of hydrophilic sugar chains. On the other hand, a water swelling polymer gel also contains a greater amount of water and is therefore in the structure similar to that of biological tissue. Hence, the gel has excellent biocompatibility. However, if the water swelling degree is too high, the physical strength of the gel is lowered. Accordingly, the swelling degree of the water swelling polymer gel A is preferably in a range of 1 to 1,000, more preferably in a range of 10 to 200, as the water absorption in weight after swelling in equilibrium provided that the dry weight of the polymer material constructing the gel is defined as 1.

The cleavable group C with the main chain to be cleaved by an enzymatic reaction, includes, without specific limitation, any such cleavable group which main chain is specifically cleaved with an enzyme present at a focal site, for example, peptide hydrolase such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolase such as phosphorylase, neuraminidase, dextranase, amylase, lysozyme, oligosaccharase and the like; oligonucleotide hydrolases such as alkaline phosphatase, endoribonuclease, endodeoxyribonuclease and the like; or an enzyme present at a focal site other than these enzymes. The cleavable group includes, for example, an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln-(Arg)$_2$-, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine and the like. Among them, amino acid or 2-mer or 6-mer oligopeptides are preferably used from the respect of the readiness of enzyme cleavage and the safety for living bodies. More preferably, use is made of the oligopeptides -Val-Pro-Arg-, -(Ala)$_2$-Pro-Val-, -Ala-Gly-Phe-, -(Ala)$_3$-, -Asp-Glu-, -(Ala)$_2$-Phe-, -(Ala)$_2$-Pro-Phe-, -Gly-Phe-Leu-Gly-, -(Arg)$_2$-, -Phe-Arg-.

The spacer B controls the reactivity of an enzyme and the cleavable group, and the spacer of itself cannot be cleaved with the enzyme. Only if the spacer serves for an enzyme present at a focal site to react with the cleavable group in an appropriate manner, the structure of the spacer is not specifically limited. However, the length of the spacer is important because it directly influences the reactivity of the cleavable group with the enzyme. If no spacer is used, the cleavage of the cleavable group is markedly decreased so that a therapeutically effective amount of the drug is hardly released from the medical polymer gel of the present invention. In other words, if use is made of a molecular chain with a less total number of carbon atoms, nitrogen atoms and oxygen atoms contained in the main chain as such a spacer, the reactivity of the enzyme and the cleavable group is lowered due to the steric hindrance of the water swelling polymer gel, causing the decrease in the release of the drug. If the total number of the atoms is below 3, the release of a therapeutically effective amount of the drug may not be expected. If the total number of the atoms is increased, the reactivity of the enzyme and the cleavable group is increased; if the total number of the atoms is above 20, the spacer may eventually take a conformation such as a turn structure and α-helix; and if the spacer takes such form, the reactivity of the enzyme and the cleavable group may be lowered. If the total number of the atoms is above 20, furthermore, the spacer may aggregate due to inter-spacer- or intra-spacer hydrophobic interaction, causing the decrease in the reactivity of the enzyme and the cleavable group. It is also possible that hyper-reactivity of the enzyme and the cleavable group may cause the release of the drug at an unnecessary level, if the total number of the atom is above 20. Therefore, preferably, the spacer is a molecular chain with the total number of carbon atoms, nitrogen atoms and oxygen atoms contained in the main chain being 4 or more; more preferably, the spacer is a molecular chain with the total being 4 to 20; and most preferably, the spacer is a molecular chain with the total being 6 to 16. A spacer with a polar group such as hydroxy group and the like elevates the reactivity of the enzyme and the clearable group, increasing the release of the drug. If the spacer is a sequencial methylene group or a sequencial ethylene oxide group, the reactivity of the enzyme and the cleavable group is increased. Because a spacer is fixed to a specific structure if it contains amide groups and cyclic groups therein, the reactivity of the enzyme and the cleavable group is likely to decrease.

The spacer includes, for example, a linear molecular chain such as a methylene chain which may or may not have a substituent, ether bond, a peptide bond, an imino bond, a C=C double bond and the like. Specific examples will be as follows: —CO—(CH$_2$)$_2$—CO—, CH$_2$—CO—NH—(CH$_2$)$_2$—NH—CO—(CH$_2$)$_2$—CO—, —CH$_2$—CH(OH)—CH$_2$—NH—CO—(CH$_2$)$_2$CO—, —CH$_2$—CH(OH)—CH$_2$—NH—(CH$_2$)$_2$—NH—CO—(CH$_2$)$_2$CO—, —NH—(CH$_2$)$_2$—NH—CO—CH$_2$—NH—CO—(CH$_2$)$_2$—CO—, —CO—(CH$_2$)$_2$—NH—CO—CH$_2$—NH—CO—(CH$_2$)$_2$—CO—, —NH—(CH$_2$)$_2$—NH—CO—CH$_2$—NH—CO—(CH$_2$)$_3$—CO—, —NH—(CH$_2$)$_2$—NH—CO—(CH$_2$)$_2$—NH—CO—(CH$_2$)$_2$—CO—, —NH—(CH$_2$)$_2$—NH—CO—CH(CH$_3$)—NH—CO—(CH$_2$)$_2$—CO—, —NH—(CH)$_2$—NH—CO—CH(CH$_2$OH)—NH—CO—(CH$_2$)—CO—.

Among them, preference is given to —NH—(CH$_2$)$_2$—NH—CO—CH$_2$—NH—CO—(CH$_2$)$_2$—CO—, —CH$_2$—CH(OH)—CH$_2$—NH—CO—(CH$_2$)$_2$CO—.

The spacer and the cleavable group with the main chain to be cleaved by an enzymatic reaction is prepared by ordinary organic synthesis. Oligopeptide is prepared by usual methods generally employed for peptide synthesis, such as solid phase synthesis and liquid phase synthesis (see for example, "Biochemistry Experimental Course, second series, No. 2, Protein Chemistry (2)," pp. 641–694, Nippon Biochemistry Association eds., issued by Tokyo Kagaku Dojin, Kabushiki Kaisha, on May 20, 1987.). Oligosaccharide is prepared by usual methods employed for synthesis and extraction of sugar chain (see for example, "New Biochemistry Experimental Course, No. 3, Sugar (I)," pp. 95–140 and pp. 421–438, Nippon Biochemistry Association eds., issued by Tokyo Kagaku Dojin, Kabushiki Kaisha, 1990.). Oligonucleic acids are prepared by usual methods generally employed for synthesis and extraction of nucleic acids, (see for example, "New Biochemistry Experimental Course, No. 2, Nucleic Acids (III)," pp. 254–269, Nippon Biochemistry Association eds., issued by Tokyo Kagaku Dojin, Kabushiki Kaisha, on May 20, 1992; "New Biochemistry Experimental Course, No. 2, Nucleic Acids (I)," pp. 147–168, Nippon Biochemistry Association eds., issued by Tokyo Kagaku Dojin, Kabushiki Kaisha, 1991).

The drug D to be used in accordance with the present invention may be selected appropriately, depending on the purpose thereof. For example, if the drug is used for wound dressings, adhesives for biological tissues, and adhesion preventing agents, the drug may be an antibacterial agent such as disinfectant and antibiotics; a blood flow modifying agent such as actosin and prostaglandin E1 (PGE1); an inflammatory and analgesic agent such as steroids and indomethacin; a growth factor such as transforming growth factor β (TGFβ), platelet-derived growth factor (PDGF), fibroblast growth factor (FGF) and the like; an enzyme inhibitor such as urinastatin, tissue inhibitor of metalloproteinase (TIMP) and the like. When the drug is used for bone reinforcing materials, the drug may be, for example, a bone cell growth factor such as bone morphogenetic protein (BMP), TGFβ, parathyroid hormone (PTE) and the like; Interleukin-1 (IL-1) inhibitor, a bone resorption suppressing factor such as bisphosphonate, calcitonin and the like. When the medical polymer gel is used for drug releasing materials, the drug may be an anticancer agent such as neocarzinostatin, adriamycin and the like; and an anti-inflammatory agent such as steroid, non-steroidal inflammatory agent and the like.

Since the drug is released from the medical polymer gel of the present invention, depending on the enzyme level generated at a focal site, the amount of the drug to be immobilized is not strictly limited. However, it is required to immobilize a minimum amount of the drug capable of exerting the therapeutic effect at a focal region. The amount of the drug in immobilization can be controlled by the ratio of introducing a spacer into a water swelling polymer gel. A too low ratio of introducing a spacer is not preferable because an effective amount of the drug cannot be immobilized. Alternatively, a too high ratio of introducing a spacer is neither preferable because the properties of the water swelling polymer gel are modified. Thus, the ratio of introducing a spacer into a water swelling polymer gel is preferably at 0.05 μmol or more, more preferably at 0.2 μmol or more to 50 μmol or less, per ml.water swelling polymer gel. The ratio of introducing a spacer should be determined, for example, by measuring the amount of the amino group in an intermediate product by the ninhydrin method (see Sarin, V. K. et al., Anal. Biochem., 117, 147–157 (1981)).

A method for immobilizing a drug, through a clearable group with the main chain to be cleaved via an enzymatic reaction and a spacer, onto a water swelling polymer gel, preferably comprises a covalent process; for example, use may be made of known activation methods and reaction methods, generally employed for immobilized enzymes and affinity chromatography. For example, a dehydration condensation method using a condensing agent such as 1-ethyl-3-(3-dimethylaminopropyl)-carbodiimide hydrochloride salt, dicyclohexylcarbodiimide and the like; a decarbonate reaction using an alkali catalyst; ammonolysis reaction of epoxy groups; ammonolysis reaction of acid anhydrides; ester exchange reaction and the like. When a cleavable group with the main chain to be cleaved via an enzyme and a drug are bound together via an ester bonding, an ether bonding or a peptide bonding, the bonding site is specifically cleaved with the enzyme to release the drug of the intact chemical structure, advantageously.

The medical polymer gel in accordance with the present invention may take an application form suitable for the objective of gel application, such as sheet, film, fiber, woven fabric, non-woven fabric, liquid, powder, sponge and the like.

By molding the medical polymer gel of the present invention into a plate form or a particle form, wound dressings may be obtained. By molding the gel as described above and then attaching the molded gel with a film made of a polyurethane resin or a silicone resin followed by addition or coating of an adhesive, wound dressings may be produced. Because the wound dressings from the medical polymer gel of the present invention are flexible due to the higher water content, less physical irritation may be induced on wounds with less pain to the patient. Furthermore, because the dressings have excellent water retentivity, the dressings may be exchanged less frequently, with the decrease in patient pain, care, and wound damage, while greatly retaining the healing promoting factor in the exudates with no inhibition of the action of the factor, advantageously.

As an additive, use may be made of pharmaceutically acceptable metal ions such as $Ca^{++}$ ion, and gel softening agents and stabilizing agents such as glycerin, polyethylene glycol (PEG) and the like, depending on the objective. The medical polymer gel of the present invention is used after appropriate preliminary swelling in physiologically acceptable solutions such as 5% glucose solution and physiological saline. Additionally, the solution may contain various pharmaceutically acceptable additives. Furthermore, if the exudates such as body fluid is at a higher level, the polymer gel may be applied in the dry state.

As to the administration thereof, the gel may be applied externally for example in the form of dressings, or adhesives, and adhesion preventing agents on wounds. If the gel is to be used as a bone reinforcing agent, the gel is administered into bone cavity, or into the cross section of a bone fracture site; if the gel is administered as a material for releasing a drug in a sustained manner, the gel is administered via subcutaneous administration, intraperitonealy administration, intraarticular administration, percutaneous administration, oral administration, intravascular administration and the like.

The present invention is characterized in that a drug is immobilized, through a cleavable group with the main chain to be cleaved with an enzymatic reaction and a spacer, onto a water swelling polymer gel, wherein the drug is bound in the form represented by the general formula (I). Thus, no satisfactory performance of the drug can be exerted if either one of the cleavable group with the main chain to be cleaved with an enzymatic reaction or the spacer is present. In other words, if a drug is immobilized using only a cleavable group with the main chain to be cleaved with an enzymatic reaction, the cleavage reaction of the cleavable group with the enzyme is very slow, so that a therapeutically effective amount of the drug cannot be released. If only the spacer is used, the drug is not successfully released at a site where the enzyme is present.

If use is made of a medical polymer gel immobilizing a drug (for example, anti-inflammatory agents, antibiotics and the like) through a cleavable group (for example, $-(Ala)_3-$, $-(Ala)_2-Pro-Val-$, $-(Ala)_2-Phe-$ and the like) to be cleaved with an enzyme (elastase and cathepsin G) generated by neutrophils, the drug is released, only at an inflammatory site infiltrated with the activated neutrophils, at an amount corresponding to the level of the enzyme present at the site, triggering the anti-inflammatory action and the antibacterial activity of the drug. Because the drug is not released at sites except the inflammatory site, the possibility of the occurrence of side effects due to the drug is remarkably decreased. If use is made of the medical polymer gel bonding an antibiotic through a cleavable group (for example, -Asp-Glu-, -Ala-Gly-Phe- and the like) to be cleaved with an enzyme (Staphylococcal serine proteinase, Staphylococcal cysteine proteinase) generated by bacteria, the antibiotic may be released only at an infected site during the development of such infection, whereby the antibacterial action is triggered. If use is made of a medical polymer gel bonding a blood flow modifying agent such as actosin, PGE1 and the like through a cleavable group (for example, $-(Ala)_2-Phe-$, $-(Ala)_2-Pro-Phe-$, -Ala-Gly-Phe-, -Phe-, -Tyr-, and the like) to be cleaved with an enzyme (cathepsin E, pepsin) which is activated under acidic conditions, the drug is released at a site with poor blood flow so as to improve the blood flow. If use is made of a medical polymer gel bonding an anticancer agent through a clearable group (for example, -Gly-Phe-Leu-Gly-, $-(Arg)_2-$, -Phe-Arg-, phosphate diester bond and the like) to be cleaved with an enzyme (alkaline phosphatase, γ-glutamyltransferase (γ-GTP), cathepsin B, cathepsin H, cathepsin L) generated by cancer cells, the drug is released only around the cancer cells, triggering the anti-cancer action. In any of the cases, the immobilized drug cannot be released at normal sites with no generation of enzymes or during the period without such generation. Therefore, side effects due to the toxicity of the drug can be suppressed at minimum.

It has been confirmed at toxicity tests that the medical polymer gel of the present invention has lower toxicity. It has been confirmed also that the stability thereof under storage is high. The medical polymer gel of the present invention is useful as the structural component for wound dressings, adhesives for biological tissues, adhesion preventing agents, bone reinforcing agents, and drug releasing materials. For treatment of inflammation and healing and promotion thereof, the gel can be applied to sites of wounds including general wounds such as scar and cut; artificial dermal defects such as dermatome wounds and dermabrasion wounds; surgery wounds such as cut wounds; burn; ulcer; and decubitus. Furthermore, the gel can be applied also to adhesion of wounds after surgery, prevention of adhesion of wounds to other tissues after surgery, bone reinforcement for osteoporosis and bone fracture, and treatment of malignant neoplasm.

Additionally, because the water swelling polymer gel (II) principally comprising a covalently crosslinked gel has a higher mechanical strength and is excellent in terms of stability and resistance to boiling water, the gel is readily sterilized. Because the gel is excellent in terms of water retentivity, the biocompatibility is also great. Additionally, the gel is so transparent that sites of wounds can be readily observed through the gel. As has been described above, the gel has such a variety of advantages that the gel is useful as wound dressings.

Under the conditions of steam sterilization (121° C. for 20 minutes), fewer substances may be solubilized from the gel. Thus, the gel is highly safe.

Since the gel is highly transparent, the conditions of wounds, i.e., the presence or absence of bacterial infection, and the proliferation status of dermis cells and epidermis cells, can be observed while the gel is attached onto the wound as a wound dressing. Thus, the gel is useful for treating and promoting the healing of general wounds such as scar, cut, acne and the like; surgery wounds such as dermatome wounds and dermabrasion wounds, and wounds such as burn, ulcer and decubitus.

Furthermore, since the gel has higher biocompatibility with less cytotoxicity, the gel is quite useful because the recovery of damaged tissues is facilitated when the gel is used as an adhesive for biological tissues and an adhesion preventing agent for the adhesion of wounds after surgery and the prevention of adhesion of wounds with tissues. Because the gel has a high stability, the gel can satisfactorily exert the objective functions over a period required for tissue adhesion and its recovery.

As the polysaccharide to be used in accordance with the present invention, use may be made of any water-soluble polysaccharide having a carboxyl group within the molecule without a functional group blocking the crosslinking reaction, preferably including a water-soluble salt of an acidic polysaccharide having a carboxyl group within the molecule, such as alginic acid and hyaluronic acid. Sodium alginate salt is most preferable because the gel prepared from the salt has good properties as the structural component of medical materials. These polysaccharides are commercially available.

Preferable molecular weight of a polysaccharide having a carboxyl group within the molecule cannot be generally determined, due to the properties of the polysaocharide, but such molecular weight is generally in a range of 100,000 to 10,000,000. From the respect of the strength of the resulting gel, the lower limit of the molecular weight of sodium hyaluronate when used as such polysaccharide is preferably 1,000,000, and more preferably 2,000,000. From the respect of handling during production, the upper limit of the molecular weight of sodium hyaluronate is preferably 10,000,000 or less. No molecular weight analysis of alginic acid has been established yet. In that case, the molecular weight is defined as the viscosity of an aqueous 1% by weight (the term "% by weight" will be abbreviated as "wt %" hereinafter) solution of sodium alginate at 20° C. Therefore, the viscosity at 20° C. of an aqueous 1 wt % solution of sodium alginate when used as a polysaccharide in accordance with the present invention is preferably 100 cp (centipoise) or more; more preferably, the viscosity should be 300 cp or more, from the respect of the strength of the resulting gel. However, the handling during production is deteriorated in that a higher viscosity requires a longer time for dissolution. Thus, the viscosity of an aqueous 1 wt % solution of sodium alginate should preferably be 1,200 cp or less.

A small number of methylene chains in a crosslinking reagent represented by the general formula (II) wherein n represents the number of methylene chains, causes ineffective crosslinking within the molecules. Alternatively, a larger number thereof causes the aggregation of the crosslinking reagent of itself or between such reagents, blocking the crosslinking reaction. Hence, n is preferably an integer of 2 to 18, and more preferably 2 to 12.

The crosslinking reagent represented by the general formula (II) may preferably form a water-soluble salt except carboxylate salt, for improving the action of promoting the crosslinking reaction and the water solubility, and for providing stability to the amino group. Carboxylate salt is not preferable because the salt blocks the crosslinking reaction. Specifically, N-hydroxysuccinimide salt is most preferable because it has excellent action of promoting the crosslinking reaction.

$R^1$ and $R^2$ independently represent hydrogen atom or a group represented by —COCH(NH$_2$)—(CH$_2$)$_4$—NH$_2$, and they determine the number of reactive groups responsible for the crosslinking of a crosslinking reagent. When both of $R^1$ and $R^2$ are hydrogen atom, the number of reactive groups responsible for the crosslinking is 2; when either $R^1$ or $R^2$ is hydrogen atom while the other is —COCH(NH$_2$)—(CH$_2$)$_4$—NH$_2$, the number of reactive groups responsible for the crosslinking is 3; when both of $R^1$ and $R^2$ are —COCH(NH$_2$)—(CH$_2$)$_4$—NH$_2$, the number of reactive groups responsible for the crosslinking is 4. Essentially, the number of reactive groups responsible for the crosslinking should be 2 or more; generally, the crosslinking is more effective as the number is larger. Because the ratio of reactive groups not involved in the crosslinking is not negligible as the number increases above 5 and additionally because the crosslinking reagent may aggregate by ionic bond together with an acidic polysaccharide, the number is preferably in a range of 2 to 4.

The salt of the crosslinking reagent represented by the general formula (II) specifically includes the salts of diaminoalkanes such as diaminoethane, diaminopropane, diaminobutane, diaminopentane, diaminohexane, diaminoheptane, diaminooctane, diaminononane, diaminodecane, diaminododecane, diaminooctadecane, etc; and the salts of mono- or di(lysyl)diaminoalkanes such as N-(lysyl)-diaminoethane, N,N'-di(lysyl)-diaminoethane, N-(lysyl)-diaminohexane, N,N'-di(lysyl)-diaminohexane, etc. For such use, preference is given to 2N-hydroxysuccinimide salt of diaminoethane, 2N-hydroxysuccinimide salt of diaminohexane, 4N-hydroxysuccinimide salt of N,N'-di(lysyl)- diaminoethane, 3N-hydroxysuccinimide salt of N-(lysyl)-diaminohexane, etc., among them.

Among the crosslinking reagents represented by the general formula (II), the diaminoalkanes can be commercially available. Mono- or dilysyl-diaminoalkanes can be synthesized by ordinary organic synthesis. For example, such synthesis is done by a process comprising of reactions the carboxyl group of lysine having the protected $\alpha$-amino group and $\epsilon$-amino group to the amino group of diaminoalkanes using a dehydration condensation agent such as carbodiimide, and thereafter removing the protective groups of the $\alpha$-amino group and the $\epsilon$-amino group; a process comprising modifying the lysine having the protected $\alpha$-amino group and $\epsilon$-amino group into an active ester with N-hydroxysuccinimide and the like, and thereafter subjecting the resulting ester to reaction with diaminoalkanes, and then removing the protective groups of the $\alpha$-amino group and the $\epsilon$-amino group. When the protective groups of the $\alpha$-amino group and the $\epsilon$-amino group are t-butyloxycarbonyl group, for example, the group is removed with trifluoroacetic acid or dioxane dissolving 4N hydrogen chloride. When the protective groups are fluorenylmethyloxycarbonyl group, the group is removed with 20% piperidine in a dimethylformamide solution. When the reaction is carried out at a ratio of the lysine having the protected $\alpha$-amino group and the $\epsilon$-amino group to diaminoalkanes being 1:1, monolysyl-diaminoalkane can be produced; when the reaction is carried out at a ratio thereof of 2:1, dilysyl-diaminoalkane can be produced. When these products are recovered in the form of a free amino group, the products are dissolved in ethyl acetate, followed by addition of N-hydroxysuccinimide at an amount equal to the amount of the amino group, to produce the salt thereof. When the products are recovered in the form of hydrochloride or trifluoroacetate salt, an aqueous solution thereof is passed through an anion exchange column equilibrated with N-hydroxysuccinimide, to obtain N-hydroxysuccinimide salt.

The crosslinking reaction of a polysaccharide having a carboxyl group within the molecule, via the crosslinking reagent represented by the general formula (II), can be effected using a dehydrogenation condensation agent such as water-soluble carbodiimide. The crosslinking reaction with such crosslinking reagent is slow when the amino group is not in the form of a salt. The crosslinking reaction of N-hydroxysuccinimide salt is so fast that the water swelling polymer gel (II) can be produced rapidly. Thus, the salt is preferable in accordance with the present invention. Even using a hydrochloride salt, the water swelling polymer gel (II) can be produced, but the gelling via the crosslinking reaction gets slow.

The crosslinking ratio can be regulated by the molar ratio of a crosslinking reagent to a polysaccharide to be used. A lower crosslinking ratio produces a more flexible gel with a higher water content. A higher crosslinking ratio produces a more rigid gel with a lower water content. The crosslinking ratio may appropriately be selected, depending on the purpose of the resulting water swelling polymer gel. No gel with a practical mechanical strength and a stability cannot be produced at a too lower crosslinking ratio, disadvantageously. Alternatively, unreactive amino groups in the crosslinking reagent may remain in the gel at a too higher molar ratio of crosslinking reagent. Thus, the reaction ratio of the crosslinking reagent represented by the general formula (II) to a polysaccharide is preferably at a ratio of 1 to 50 mole %, more preferably at a ratio in a range of 10 to 40 mole % to the carboxyl group of the polysaccharide.

The crosslinking ratio can be regulated by the molar ratio of a crosslinking reagent to a polysaccharide to be used, and is determined by elemental analysis or NMR. When use is made of a polysaccharide without nitrogen atoms, such as alginic acid and hyaluronic acid, the crosslinking ratio can be determined by the elemental analysis of nitrogen atoms in the recovered gel. Also, the crosslinking ratio can be determined, by analyzing the resulting gel by proton NMR and determining the ratio of the signal intensities of the methine proton of the polysaccharide and the methylene proton of the crosslinking reagent.

The water swelling polymer gel (II) of the present invention of itself has practical strength and stability, but the gel can be used in combination with other gelling methods including crosslinkings via ionic bond and/or hydrophobic bond.

The water swelling polymer gel (II) of the present invention has a higher water retentivity and a lower antigenicity because the gel comprises a polysaccharide; and the gel is readily absorbed and excreted even if the gel is left in living bodies because the raw materials of the crosslinking reagent are compounds to be administered biologically. Accordingly, the gel has superior biocompatibility and safety.

To the water swelling polymer gel (II) of the present invention may be added pharmaceutically acceptable additives, for example, inorganic ions such as $Na^+$, $Ca^{++}$, $Mg^{++}$, etc.; polyvalent alcohols such as ethylene glycol, propylene glycol, glycerin, PEG, etc.; polymer compounds such as polyvinyl alcohol, polyacrylic acid, etc., for the purpose of controlling the water retention and providing viscosity. Also, pharmaceutical agents and physiologically active substances may be added, including disinfectants, antibiotics, antibacterial agents, blood flow modifying agents such as actosin and PGE1, growth factors such as TGF$\beta$, PDGF and FGF, enzyme inhibitors such as urinastatin and TIMP, steroidal and non-steroidal anti-inflammatory agents, and structural components such as fibrin and collagen.

The water swelling polymer gel (II) of the present invention is useful as the structural component for medical materials such as wound dressings, adhesives for biological tissues, and adhesion preventing materials.

By molding the water swelling polymer gel (II) of the present invention into the form of plate or particles, wound dressings can be prepared. By molding the gel as described above and thereafter attaching film of a polyurethane resin and silicone resin to the molded gel and adding or coating an adhesive onto the film, wound dressings may be prepared. Wound dressings prepared from the water swelling polymer gel (II) of the present invention is so advantageous for the observation of wounds due to the higher transparency. Because the gel with a higher water retentivity is flexible, the gel has less physical irritation to wounds, causing less pain to patients. Because the gel has good water retentivity and is not soluble in body fluid and the like, furthermore, the wound dressings may be exchanged less frequently, with the decrease in patient pain, care, and wound damage due to the exchange of the dressings. The dressings may satisfactorily retain the healing promoting factor in the exudates, advantageously without inhibiting the action. The dressings are highly safe because the dressings can be subjected to steam sterilization.

By molding the water swelling polymer gel (II) of the present invention in the form of plate, woven fabric, non-woven fabric, particles, sponge and the like, adhesion preventing materials can be produced. By molding the gel as described above and thereafter mixing glycerin, PEG and the like with the molded gel or dispersing them into the gel, adhesion preventing materials may be produced.

By molding the water swelling polymer gel (II) of the present invention in the form of plate, woven fabric, non-woven fabric, particles, sponge and the like, adhesives for biological tissues can be produced. By molding the gel as described above and thereafter mixing dextran, pullulan, fibrin, collagen and the like with the molded gel or dispersing them into the gel, adhesives for biological tissues may be produced.

Because the water swelling polymer gel (II) of the present invention has greater resistance to boiling water, the gel has less soluble matters and has low toxicity at toxicity tests.

DESCRIPTION OF THE PREFERRED EMBODIMENTS

The present invention will now be explained specifically in examples, reference examples, comparative examples and test examples. The present invention is not limited to these examples.

EXAMPLE 1

N-hydroxysuccinimide (2.3 g (20 mmol); HOSu, manufactured by Peptide Institute, Inc.) was dissolved in ethyl acetate (150 ml), followed by dropwise addition of ethylenediamine (EDA) (0.6 g (10 mmol); Wako Junyaku Industry, Kabushiki Kaisha) dissolved in ethyl acetate (10 ml) under agitation at room temperature. After completion of dropwise addition, agitation was continued for another one hour. The precipitated crystal was filtered, followed by drying under reduced pressure, to obtain ethylenediamine 2N-hydroxysuccinimide (EDA.2HOSu; 2.9 g). Yield; about 100%.

EDA.2HOSu (0.20 g (0.7 mmol)) and 1-ethyl-3-(3-dimethylaminopropyl)-carbodiimide hydrochloride (0.96 g (5 mmol), manufactured by Peptide Institute, Inc.; EDC.HCl) were dissolved in an aqueous 1 wt % solution (30 ml; 1.5 mmol of carboxyl group) of sodium alginate (at 500 to 600 cp, manufactured by Wako Junyaku Industry, Kabushiki Kaisha), which was then cast into a 12 cm×8 cm-polystyrene tray and was then left therein at room temperature. About 15 hours later, a water swelling polymer gel was obtained.

EXAMPLE 2

EDA.2HOSu (0.05 g (0.175 mmol)) and EDC.HCl (0.96 g (5 mmol)) were dissolved in an aqueous 1 wt % solution (30 ml; 1.5 mmol of carboxyl group) of sodium alginate (at 500 to 600 cp; Wako Junyaku Industry, Kabushiki Kaisha), which was then cast into a 12 cm×8 cm-polystyrene tray and was then left therein at room temperature. About 15 hours later, a water swelling polymer gel was obtained.

EXAMPLE 3

EDA.2HOSu (0.80 g (2.8 mmol)) and EDC.HCl (0.96 g (5 mmol)) were dissolved in an aqueous 1 wt % solution (30 ml; 1.5 mmol of carboxyl group) of sodium alginate (at 500 to 600 cp; Wako Junyaku Industry, Kabushiki Kaisha), which was then cast into a 12 cm×8 cm-polystyrene tray and was then left therein at room temperature. About 15 hours later, a water swelling polymer gel was obtained.

EXAMPLE 4

HOSu (2.3 g (20 mmol)) was dissolved in ethyl acetate (150 ml), followed by dropwise addition of hexamethylenediamine (1.2 g (10 mmol); HDA, manufactured by Wako Junyaku Industry, Kabushiki Kaisha) dissolved in ethyl acetate (10 ml), under agitation at room temperature. After completion of dropwise addition, agitation was continued for another one hour. The precipitated crystal was filtered, followed by drying under reduced pressure, to obtain hexamethylenediamine 2N-hydroxysuccinimide (HDA.2HOSu; 3.3 g). Yield; about 96%.

HDA.2HOSu (0.24 g (0.7 mmol)) and EDC.HCl (0.96 g (5 mmol)) were dissolved in an aqueous 1 wt % solution (30 ml; 1.5 mmol of carboxyl group) of sodium alginate (at 500 to 600 cp; manufactured by Wako Junyaku Industry, Kabushiki Kaisha), which was then cast into a 12 cm×8 cm-polystyrene tray and was then left therein at room temperature. About 15 hours later, a water swelling polymer gel was obtained.

EXAMPLE 5

EDA.2HCl (93 mg (0.7 mmol); manufactured by Wako Junyaku Industry, Kabushiki Kaisha) and EDC.HCl (0.96 g (5 mmol)) were dissolved in an aqueous 1 wt % solution (30 ml; 1.5 mmol of carboxyl group) of sodium alginate (at 500 to 600 cp; manufactured by Wako Junyaku Industry, Kabushiki Kaisha), which was then cast into a 12 cm×8 cm-polystyrene tray and was then left therein at room temperature. About 4 days later, a water swelling polymer gel was obtained.

EXAMPLE 6

$N^\alpha$-fluorenylmethoxycarbonyl-$NH^\epsilon$-t-butyloxycarbonyl-L-lysine (Fmoc-Lys(Boc); 4.7 g (0.01 mol); Peptide Institute, Inc.) and HOSu (1.15 g (0.01 mol)) were dissolved in ethyl acetate (50 ml), followed by addition of dicyclohexylcarbodiimide (DCC; 1.7 g (0.011 mol); Peptide Institute, Inc.) under agitation in ice cooling, and subsequent agitation was done in ice cooling for another one hour and overnight agitation was carried out at room temperature. Filtering the insoluble matters off, the filtrate was concentrated under reduced pressure to obtain crystal, which was then recrystallized in isopropyl alcohol-ethyl acetate. The crystal was dried under reduced pressure to obtain $NH^\alpha$-fluorenylmethoxycarbonyl-$NH^\epsilon$-t-butyloxycarbonyl-L-lysyl-N-hydroxysuccinimide ester (Fmoc-Lys(Boc)-OSu).

Fmoc-Lys(Boc)-OSu (2.82 g (5 mmol)) was dissolved in ethyl acetate (50 ml), followed by dropwise addition of a solution (10 ml) of ethylenediamine (0.15 g (2.5 mmol)) dissolved in ethyl acetate, under agitation at room temperature. After completion of dropwise addition, agitation was further continued overnight. Filtering the precipitated crystal and drying the crystal under reduced pressure, N,N'-($N^\alpha$-fluorenylmethoxycarbonyl-$NH^\epsilon$-t-butyloxycarbonyl-L-lysyl)-ethylenediamine ((Fmoc-Lys(Boc))$_2$-EDA) was obtained. Yield; 100%.

The total amount of the obtained (Fmoc-Lys(Boc))$_2$-EDA was suspended in dioxane (200 ml), followed by addition of piperidine (40 ml; Wako Junyaku Industry, Kabushiki Kaisha) and agitation at room temperature for one hour. The crystal obtained via concentration under reduced pressure was washed in diethyl ether, to obtain N,N'-di($NH^\epsilon$-t-butyloxycarbonyl-L-lysyl)-ethylenediamine ((Lys(Boc))$_2$-EDA). The recovered ((Lys(Boc)$_2$-EDA) in total was dissolved in trifluoroacetic acid (TFA; 10 ml; Peptide Institute, Inc.) followed by agitation at room temperature for 2 hours. The crystal obtained via concentration under reduced pressure was washed in diethyl ether, followed by drying under reduced pressure, to obtain N,N'-di(L-lysyl)- ethylenediamine trifluoroacetic acid salt ((Lys)$_2$-EDA.4TFA). The (Lys)$_2$-EDA.4TFA in total was dissolved in distilled water (50 ml), and was subsequently passed through a column packed with diethylaminoethyl cellulose (DE52, Whatman; 20 g) equilibrated with an aqueous 1M HOSu solution. Then, the eluate was concentrated under reduced pressure, to obtain N,N'-di(L-lysyl)-ethylenediamine N-hydroxysuccinimide salt ((Lys)$_2$-EDA.4HOSu; 0.78 g). Yield; 40%.

(Lys)$_2$-EDA.4HOSu (0.29 g; 0.375 mmol) and EDC.HCl (0.96 g; 5 mmol) were dissolved in an aqueous 1 wt % solution (30 ml; 1.5 mmol of carboxyl group) of sodium alginate (at 500 to 600 cp; Wako Junyaku Industry, Kabushiki Kaisha), and the resulting solution was cast into a 12 cm×8 cm-polystyrene tray and was then left therein to stand at room temperature. About 15 hours later, a water swelling polymer gel was obtained.

EXAMPLE 7

In an aqueous 1 wt % solution (60 ml) of sodium hyaluronate (Seikagaku Kogyo, Kabushiki Kaisha) were dissolved (Lys)$_2$-EDA.4HOSu (0.29 g (0.375 mmol)) and EDC.HCl (0.96 g (5 mmol)), and the resulting solution was cast in a 12 cm×8 cm-polystyrene tray and was then left therein to stand at 4° C. About 48 hours later, a water swelling polymer gel was obtained.

Reference Example 1

The water swelling polymer gels produced in Examples 1 to 4 and 6 were sufficiently washed in an aqueous solution (ECF) dissolving CaCl$_2$ and NaCl at the same concentrations as those of the intercellular fluid (Ca ion of 5 meq and Na ion of 143 meq). Subsequently, the gels were immersed in 50% glycerin-physiological saline, followed by steam sterilization (at 121° C. for 20 minutes) to prepare transparent wound dressings of sheet type.

Reference Example 2

The water swelling polymer gels produced in Examples 1 and 4 and 6 were sufficiently washed in ECF, and were attached with polyurethane sheet coated with a polymethacrylate ester adhesive, followed by steam sterilization (at 121° C. for 20 minutes) to prepare transparent wound dressings of sheet type.

Reference Example 3

The water swelling polymer gels produced in Examples 1 and 4 and 6 were sufficiently washed in ECF, followed by steam sterilization (at 121° C. for 20 minutes). The gels were immersed in an aqueous 1 mg/ml gentamycin solution sterilized by filtration, to prepare wound dressings containing gentamycin.

Reference Example 4

The water swelling polymer gel produced in Example 7 was sufficiently washed in pure water, followed by freeze-drying to prepare sponge-like sheet. The sheet was subjected to γ-ray sterilization to prepare an adhesion preventing material.

Reference Example 5

The water swelling polymer gel produced in Example 7 was sufficiently washed in physiological saline, followed by freeze-drying to prepare sponge-like preparation for γ-ray sterilization. Together with an equal amount of sterilized acidic aqueous solution of 0.5 wt % collagen (Koken Kabushiki Kaisha), the preparation was aseptically ground in ice cooling to prepare a transparent slurry adhesive for biological tissues.

Comparative Example 1

EDA (42 mg (0.7 mmol); Wako Junyaku Industry, Kabushiki Kaisha) and EDC.HCl (0.96 g (5 mmol)) were dissolved in an aqueous 1 wt % solution (30 ml; 1.5 mmol of carboxyl group) of sodium alginate (at 500 to 600 cp; Wako Junyaku Industry, Kabushiki Kaisha), which was then cast into a 12 cm×8 cm-polystyrene tray and was then left therein at room temperature. Even 8 days later, no water swelling polymer gel was obtained.

Comparative Example 2

An aqueous 1 wt % solution (30 ml) of sodium alginate (at 500 to 600 cp; Wako Junyaku Industry, Kabushiki Kaisha) was cast into a 12 cm×8 cm-polystyrene tray, followed by overlaying thereon an aqueous 1% calcium chloride solution, which was then left as it was for one day to prepare a semi-transparent water swelling polymer gel of sheet type.

Comparative Example 3

In an aqueous 0.01N hydrochloric acid solution (30 ml) of 1 wt % chitosan 500 (Wako Junyaku Industry, Kabushiki Kaisha) was dissolved HOSu (47 mg (0.3 mmol)), followed by addition of t-butyloxycarbonyl-L-glutamic acid (74 mg (0.3 mmol)) and EDC.HCl (0.96 g (5 mmol)). The resulting mixture was cast in a 12 cm×8 cm-polystyrene tray and was left therein at room temperature. About 24 hours later, a water swelling polymer gel was obtained.

Comparative Example 4

Under agitation while ice cooling, succinic anhydride (3 g; Wako Junyaku Industry, Kabushiki Kaisha) was added to and reacted with an aqueous solution (30 ml) of 10 wt % dextran (molecular weight of 100,000 to 200,000; manufactured by Wako Junyaku Industry, Kabushiki Kaisha) while keeping the pH to 8 to 9 with aqueous 5N NaOH solution. After consumption of about 6 ml of the aqueous 5N NaOH solution, the pH was adjusted to 4 with glacial acetic acid. Then, the resulting solution was dialyzed against water at 4° C. for 2 days. After concentrating the solution to a final volume of 20 ml at a temperature below 50° C., the concentrated solution was cast in a 8 cm×8 cm-glass plate and was then heated at 60° C. for 2 hours and subsequently at 120° C. for one hour, to prepare succinate crosslinked dextran of film type. Immersing the dextran in ECF, a water swelling polymer gel was obtained. While water swelling, the gel was decomposed into pieces below several centimeters. Under observation, the resulting gel was colored and fragile, and was further decomposed into pieces when held with forceps and the like.

Test Example 1

The water swelling polymer gels produced in Example 2 and Comparative Examples 2 to 4 were sufficiently washed in ECF, for carrying out the following tests. The results are collectively shown in Table 1.

Handling

Each of the water swelling polymer gels was cut into pieces of about 2-cm square. Then, handling with dental forceps was assessed.

Flexibility

Each of the water swelling polymer gels was cut into pieces of about 2-cm square. While picking up one end of the pieces with dental forceps or a spatula, it was observed whether or not the end could be bent while in contact with the other end.

Thermal resistance

Each of the water swelling polymer gels was cut into pieces of about 2-cm square, which were then subjected to steam sterilization (at 121° C. for 20 minutes) in physiological saline. Observation was done about the appearance prior to and after the sterilization, as well as the change in handling.

Compression performance

Each of the water swelling polymer gels was cut into pieces of about 3-cm square and a thickness of 0.3 cm. The pieces were placed on a stainless-steel desk top. Then, the pieces were pressed gradually from the upper part with a polypropylene device of a bottom having an about 1-cm diameter and plain face. Measuring the distortion and stress until the gel was broken, the value of the initial stress/distortion and the fracture strength were determined. Furthermore, when the two values were kept in an almost linear relation up to the breaking point, the gel was designated elastic body; when the values were kept in a non-linear relation, the gel was designated viscous elastic body.

Transparency

Each of the water swelling polymer gels was packed tightly in a photo-cell of an optical path of 1 cm for measuring absorbance, and the transparency was determined by a Beckman Type Du-65 spectrophotometer at 400 nm.

Water absorption ratio

The water absorption ratio of each of the water swelling polymer gels was determined as the ratio of the weight after water absorption to the dry weight.

Solubility

To a 1 g portion of each of the water swelling polymer gels was added 10 ml distilled water for injection, and the resulting suspension was left to stand at 37° C. for 15 hours. The solubility of each of the water swelling polymer gels was determined on the basis of the extent at which the supernatant passed through a 0.22-μm pore size filter (MILLEX GV, manufactured by Millipore, Inc.).

Durability

Each of the water swelling polymer gels was cut into pieces of about 2-cm square, and was then heated in PBS (10 mM phosphate buffer, pH 7.4, containing 0.15M NaCl) at 37° C. under shaking at 160 cycles per minute for 24 hours. The change in appearance and strength prior to and after shaking was determined.

Cytotoxicity test

Distilled water for injection (10 ml) was added to each (1 g) of the water swelling polymer gels, which was then left to stand at 37° C. for 15 hours. The supernatant was sterilized by filtration (MILLEX GV, manufactured by Millipore Inc.), and to a 5-ml portion thereof were added calf fetus serum (1 ml) and a 2.25-fold concentrated Eagle MEM medium (4 ml; Nissui Pharmaceutical Co., Ltd.), followed by suspension of a cell strain L929 (ATCC CCL1, NCTC clone 929) to 30,000 cells/ml. At 100 μl/well, the resulting suspension was divided in a 96-well U-bottom plate manufactured by Nunk Co., Ltd. In the presence of 5% $CO_2$, the plate was subjected to culture at 37° C. for 3 days. Subsequently, the number of living cells in each well was counted by a fluorescent method using propidium iodide (see Bruning, J. W., Automated reading of HLA-A, B, C typing and screening. The propidium iodide method. Hum Immunol., 5, 225–231 (1982)). The results were compared, with those of controls using distilled water for injection without containing the water swelling polymer gels.

Results

As apparently shown in Table 1, the water swelling polymer gel produced in Example 2 can satisfy all the requirements demanded for the water swelling polymer gel as the structural component of medical materials. Thus, it is shown that the gel can satisfy the objective.

Text Example 2

In the same manner as in Reference Example 2, the water swelling polymer gels produced in Example 2, and Comparative Examples 2 and 3, were prepared in sheet-type wound dressings.

Eight partial thickness wounds in total, each of 5 cm×5 cm, were prepared on the back of a pig. Then, the sheet-type wound dressings of Example 2 and Comparative Examples 2 or 3 were individually attached to adjacent wounds for 7 days. The above test was so-called half-side test, and the test was carried out on two pairs.

Results

For comparing the sheet-type wound dressings of Example 2 with the sheet-type wound dressings of Comparative Example 2 on two pairs of sample wounds, the sheet-type wound dressings of Example 2 were more transparent than the sheet-type wound dressings of Comparative Example 2 during the test period. On day 7, the sheet-type wound dressings of Example 2 showed better healing tendency. Furthermore, the sheet-type wound dressings of Comparative Example 2 tended to dissolve during their attachment on the wounds.

For comparing the sheet-type wound dressings of Example 2 with the sheet-type wound dressings of Comparative Example 3, no significant difference was observed in the healing tendency and transparency on day 7. However, it was observed that the sheet-type wound dressings of Comparative Example 3 were liquefied several minutes after their attachment onto the wounds. From the following respect, the liquefaction of wound dressings is a significant fault. Specifically, the possibility of bacterial infection due to the leakage is very high, and once infected, the wounds may turn into a medium for bacteria involving a high risk and the contamination of clothes and beds with a higher possibility of the enlargement of bacterial infection in the environment. This is a critical concern in clinical practice. So as to evade such possibility, wound dressings should be exchanged more frequently, but wounds may be damaged with the increase in patient pain and care via the exchange of the dressings. Because the healing promoting factors kept in the exudates may be lost every such exchange, the greatest advantage of an occlusive wound dressing cannot be exerted.

At any test, the sheet-type wound dressings of Example 2 showed better healing ratios and transparency than those of the controls, with no tendency of liquefaction.

EXAMPLE 8

According to the following method, it was prepared a medical polymer gel (see the formula below (III)) comprising alginate gel as the water swelling polymer gel, —NH—$(CH_2)_2$—NH—CO—$CH_2$—NH—CO—$(CH_2)_2$—CO—as the spacer, -$(Ala)_2$-Pro-Val- as the cleavable group and Mafenide as the drug.

Alginate (CO)—NH—(CH₂)₂—NH—CO—CH₂—NH—CO—(CH₂)₂—CO—(Ala)₂—Pro—Val⏋ (III)

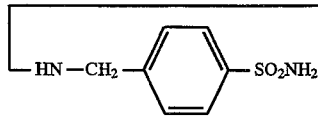
⌊HN—CH₂—⟨benzene⟩—SO₂NH₂

A 2.3 g (20 mmol) portion of N-hydroxysuccinimide (HOSu, Peptide Institute, Inc.) was dissolved in ethyl acetate (150 ml), followed by dropwise addition of ethylenediamine (0.6 g (10 mmol); manufactured by Wako Junyaku Industry, Kabushiki Kaisha) dissolved in ethyl acetate (10 ml), under agitation at room temperature. After completion of dropwise addition, agitation was continued for another hour. The precipitated crystal was filtered and dried under reduced pressure, to obtain ethylenediamine 2N-hydroxysuccinimide (EDA.2HOSu; 2.9 g). Yield; about 100%.

To an aqueous 1 wt % solution (100 ml) of sodium alginate (at 100 to 150 cp; manufactured by Wako Junyaku Industry, Kabushiki Kaisha) were added the HOSu salt of N-(t-butyloxycarbonylglycyl)ethylenediamine (Boc-Gly-EDA-HOSu; 0.11 g (0.33 mmol), Peptide Institute, Inc.) and 1-ethyl-3-(3-dimethylaminopropyl)carbodiimide hydrochloride salt (EDC.HCl, 0.19 g(1 mmol), Peptide Institute, Inc.), for overnight agitation at 4° C. The resulting aqueous solution was added dropwise to 200 ml of trifluoroacetic acid (TFA, Peptide Institute, Inc.), for agitation at room temperature for one hour. The resulting precipitate was washed sufficiently in methanol, and dried under reduced pressure to obtain Algin-EDA-Gly. The amount of the introduced amino group was determined by the ninhydrin method, which was 20 μmol/g (0.2 μmol/ml when corrected per 1 wt % gel).

The UV absorption spectrum of the resulting Algin-EDA-Gly in an aqueous 0.05M NaHCO₃ solution was measured at 220 nm to 400 nm, by a Beckman Type Du-65 spectrophotometer using a cell of a 1-cm optical path for measuring absorbance. The results are shown in FIG. 1.

Boc-(Ala)₂-Pro-Val (46 mg (0.1 mmol)) produced by liquid phase synthesis and Mafenide hydrochloride salt (22 mg (0.1 mmol); Sigma) were dissolved in dimethylformamide (DMF), followed by addition of hydroxybenzotriazole (HOBt; 14 mg (0.1 mmol); Peptide Institute, Inc.), EDC.HCl (95 mg (0.5 mmol)) and triethylamine (14 μl (0.1 mmol)) for agitation under ice cooling for one hour and subsequent agitation at room temperature overnight. Adding water, insoluble matters in precipitated were filtered, washed in water, and dried under reduced pressure to obtain Boc-(Ala)₂-Pro-Val-Mafenide (35 mg). Yield; 50%.

The resulting Boc-(Ala)₂-Pro-Val-Mafenide in total was dissolved in 10 ml of TFA containing 5% water, and was then left to stand at room temperature for one hour, followed by precipitation with diethyl ether to obtain (Ala)₂-Pro-Val-Mafenide. The resulting (Ala)₂-Pro-Val-Mafenide in total was dissolved in DMF, followed by addition of succinic anhydride (15 mg (0.15 mmol)) and overnight agitation at room temperature, to obtain Suc-(Ala)₂-Pro-Val-Mafenide (about 20 mg).

To an aqueous 0.05M NaHCO₃ solution (5 ml) of 1 wt % Algin-EDA-Gly were added Suc-(Ala)₂-Pro-Val-Mafenide (7 mg (10 μmol)) and EDC.HCl (95 mg (0.5 mmol) for overnight agitation at 4° C. Furthermore, EDA.2HOSu (11 mg (38 μmol)) and EDC.HCl (0.19 g (1 mmol)) were added to and dissolved in the mixture, and the resulting mixture was cast into a petri dish of a 3-cm diameter and subsequently left therein at room temperature for one day, for gelling. The resulting gel was sufficiently washed in pure water for substitution with ethanol, followed by aseptic sterilization under reduced pressure to prepare a dry-sheet-type medical polymer gel.

EXAMPLE 9

According to the following method, it was prepared a medical polymer gel (see the formula below (IV)) comprising PVA gel as the water swelling polymer gel, —CH₂—CH(OH)—CH₂—NH—CO—(CH₂)₂CO—as the spacer, -Ala-Gly-Phe- as the cleavable group and acrinol (ACR) as the drug.

PVA(O)—CH₂—CH(OH)—CH₂—NH—CO—(CH₂)₂CO—Ala—Gly—Phe⏋ (IV)

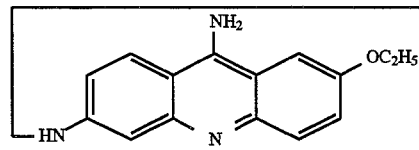

An aqueous 2 wt % PVA (average polymerization degree of 17,900; saponification degree of 99.9%; 53% of syndiotacticity by Diad expression) solution was added dropwise to n-hexane cooled to −70° C., under agitation, for repeating two cycles of melting at room temperature and freezing at −70° C., to obtain PVA gel beads. The resulting PVA gel beads were washed sufficiently in acetone followed by drying under reduced pressure. The dried PVA gel beads (20 g) were suspended in a mixture solution of 50 ml of aqueous 0.5N NaOH solution and 50 ml of dioxane, for reaction with 10 ml of epichlorohydrin at about 40° C. for 2 hours, to obtain epoxylated PVA gel beads. After washing, the beads were suspended in 25% aqueous ammonia solution (100 ml), for reaction at about 40° C. for 2 hours, to obtain aminated PVA gel beads. The resulting aminated PVA gel beads were sufficiently washed in acetone, for drying under reduced pressure. The amount of the introduced amino group was determined by the ninhydrin method, which was 50 μmol/g (1 μmol/ml when corrected per 2 wt % gel).

In the same manner as in Example 8 except that use was made of Boc-Ala-Gly-Phe instead of Boc-(Ala)₂-Pro-Val and that use was made of acrinol (ACR, Wako Junyaku Industry, Kabushiki Kaisha) instead of Mafenide, Suc-Ala-Gly-Phe-ACR was obtained.

Aminated PVA gel beads (100 mg) were suspended in an aqueous 0.05M NaHCO$_3$ solution (10 ml), followed by addition of Suc-Ala-Gly-Phe-ACR (6 mg (10 μmol)) and EDC.HCl (96 mg (0.5 mmol)) for overnight agitation at 4°

$(CH_2)_2$—NH—CO—$CH_2$—NH—CO—$(CH_2)_2$—CO—as the spacer, -Ala-Ala-Phe- as the cleavable group and Norfloxacin (NFLX) as the drug.

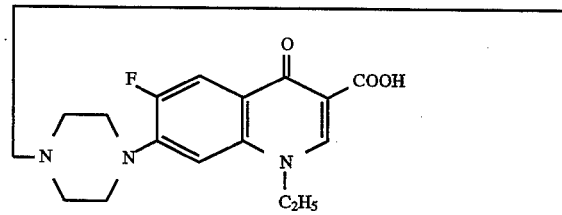

C. After sufficient washing by water, ethanol substitution and aseptic drying under reduced pressure yielded a medical polymer gel in beads.

EXAMPLE 10

According to the following method, it was prepared a medical polymer gel (see the formula below (V)) comprising PVA gel as the water swelling polymer gel, —CH$_2$CH(OH) —CH$_2$—NH—CO—(CH$_2$)$_2$CO—as the spacer, -Ala-Ala-Phe- as the clearable group and gentamycin (GM) as the drug.
PVA(O)-CH$_2$CH(OH)-CH$_2$-NH—CO-(CH$_2$)$_2$CO-Ala-Ala-Phe-(NH)GM+tm (V)

As in Example 9, an aqueous 2 wt % PVA solution (30 ml) was cast in a 10 cm×10 cm-glass plate, and then was left to stand overnight at –20° C. for freezing. Furthermore, two cycles of melting at room temperature and freezing at –20° C. were carried out, to obtain PVA gel sheet. In the same manner as in Example 9, amino groups were introduced into the resulting PVA gel sheet. The amount of the introduced amino group was determined by the ninhydrin method, which was 20 μmol/ml. The aminated PVA gel sheet was shaken overnight together with succinic anhydride (1 g) in dioxane (100 ml), followed by washing in water to obtain PVA gel sheet introduced with carboxyl groups. Because no amino group was detected by the ninhydrin method, the calculated amount of the carboxyl group introduced was 20 μmol/ml. Furthermore, the PVA gel sheet introduced with carboxyl groups was shaken overnight at room temperature in dioxane (100 ml), together with HOSu (0.23 g (2 mmol)) and DCC (0.4 g (2 mmol)). After sufficient washing in methanol, 10 mM phosphate buffer (PB; 10 ml), pH 7.4 dissolving -Ala-Ala-Phe- (74 mg (0.2 mmol)) synthesized by the solid phase method, was added to the resulting mixture, for shaking overnight at 4° C. After sufficient washing by PB, gentamycin sulfate (GM, Sigma; 0.37 g (0.5 mmol)) and EDC.HCl (0.38 g (2 mmol)) were added to the buffer, followed by overnight agitation at 4° C. After sufficient washing by PB, a sheet-type medical polymer gel was obtained.

EXAMPLE 11

According to the following method, it was prepared a medical polymer gel (see the formula below (VI)) comprising alginate gel as the water swelling polymer gel, —NH—

To an aqueous 1 wt % solution (100 ml) of sodium alginate (at 500 to 600 cp; Wako Junyaku Industry, Kabushiki Kaisha) were added then Boc-Gly- EDA.HOSu (0.11 g(0.33 mmol)) and EDC.HCl (0.96 g (5 mmol)) for overnight agitation at 4° C. The resulting aqueous solution was dropwise added into TFA (200 ml), for agitation at room temperature for one hour. Insoluble matters were sufficiently washed in methanol and dried under reduced pressure to obtain Algin-EDA-Gly. The amount of the introduced amino group was determined by the ninhydrin method, which was 55 μmol/g (0.55 μmol/ml when corrected per 1 wt % gel).

The UV absorption spectrum of the resulting Algin-EDA-Gly in aqueous 0.05M NaHCO$_3$ solution at 220 nm to 400 nm is almost the same as shown in FIG. 1.

The resulting Algin-EDA-Gly was dissolved in an aqueous 0.05M NaHCO$_3$ solution to a final concentration of 1 wt %. To the resulting solution (10 ml) was added succinic anhydride (5 mg (50 μmol)) under agitation and ice cooling, followed by dropwise addition of an aqueous 5N NaOH solution to retain the pH around 7. About 2 hours later, the pH did not decrease any more. Dialyzing the resulting reaction solution against pure water at 4° C. for 2 days, Algin-EDA-Gly-Suc was obtained. The amount of the remaining amino group was determined by the ninhydrin method, which was 4 μmol/g; the amount of the carboxyl group introduced was calculated to be 0.51 μmol/ml when corrected per 1 wt % gel.

Figure 2:
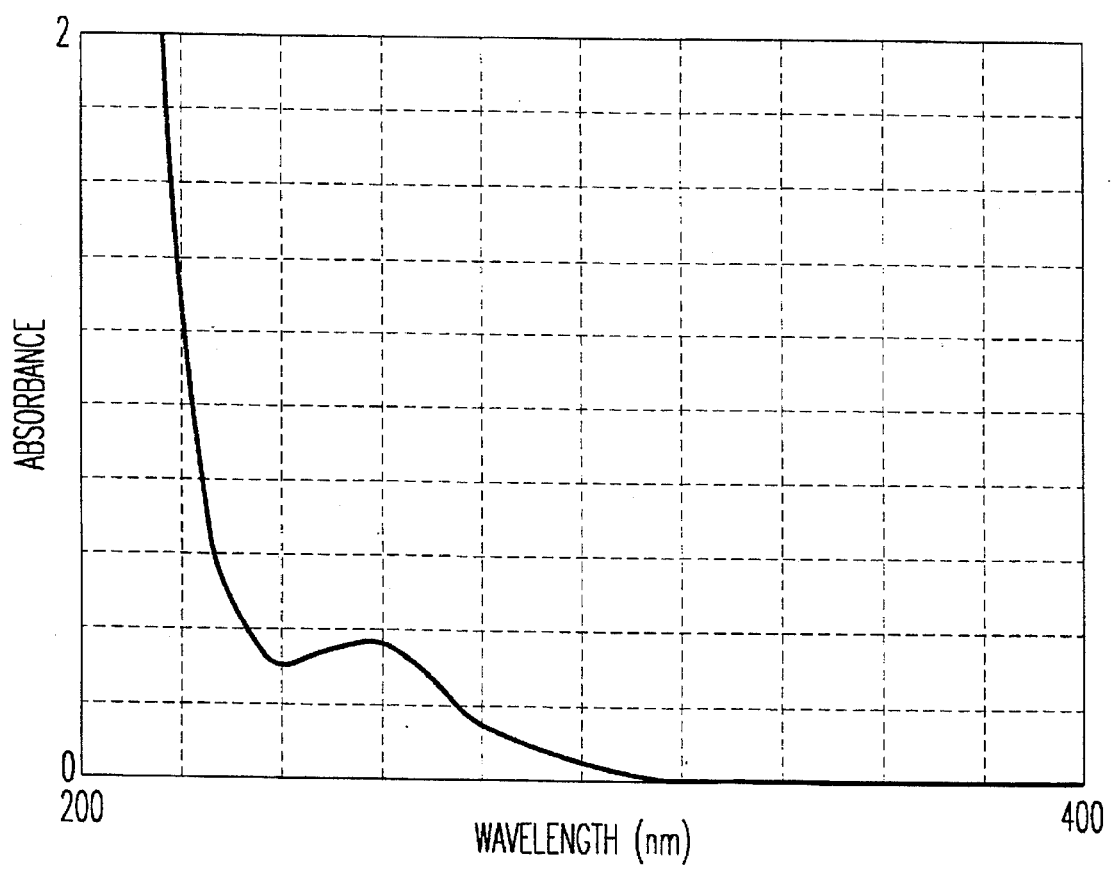
FIG. 2 depicts the UV absorption spectrum chart of the Algin-EDA-Gly-Suc-Ala-Ala-Phe of Example 11 after 10-fold dilution in distilled water.

To an aqueous 1 wt % Algin-EDA-Gly-Suc solution (10 ml) were added HOSu (5 mg; 40 μmol) and EDC.HCl (40 mg; 200 μmol), followed by overnight agitation at 4° C. to obtain Algin-EDA-Gly-Suc-OSu. To the resulting reaction solution was added Ala-Ala-Phe (13 mg; 40 μmol) synthesized by the solid phase synthesis and dissolved in PB (1 ml), followed by agitation overnight at 4° C. The reaction solution was dialyzed against pure water for 2 days, to obtain Algin-EDA-Gly-Suc-Ala-Ala-Phe. The resulting Algin-EDA-Gly-Suc-Ala-Ala-Phe was diluted by 10 fold with pure water for measuring the UV absorption spectrum, which is shown in FIG. 2. The absorption originated from the phenyl group of phenylalanine is observed at 258 nm.

Figure 3:
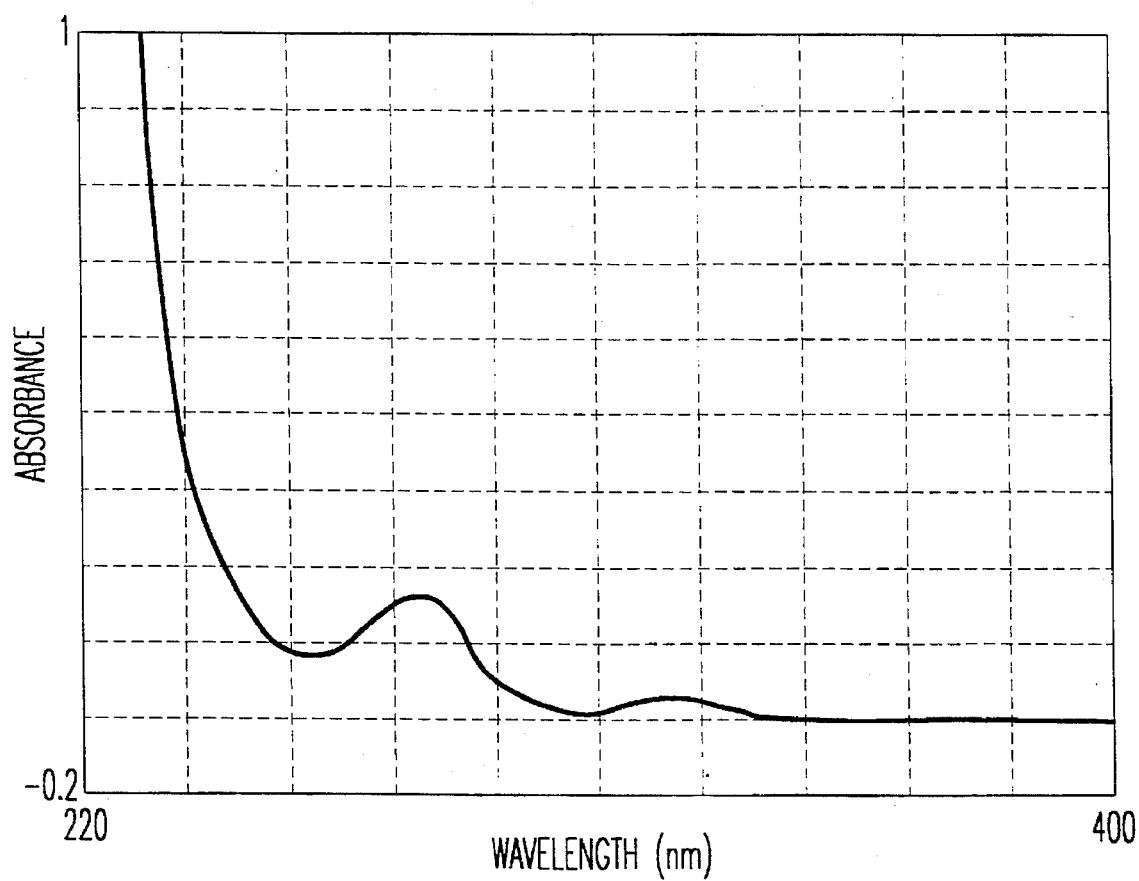
FIG. 3 depicts the UV absorption spectrum chart of the medical polymer gel of Example 11.

To the total amount of the resulting Algin-EDA-Gly-Suc-Ala-Ala-Phe were added HOSu (5 mg; 40 μmol) and EDC.HCl (40 mg; 200 μmol) for overnight agitation at 4° C. Furthermore, Norfloxacin (13 mg (36 μmol); NFLX, Sigma) dissolved in dimethyl sulfoxide (1 ml; DMSO) was added to the solution and stand for overnight agitation at 4° C. To the resulting mixture EDA.2HOSu (22 mg; 76 μmol) and EDC (155 mg; 1 mmol) were added, and the resulting solution was cast into a petri dish of a 8-cm diameter and was left therein at room temperature for one day for gelling. The resulting gel was sufficiently washed with physiological saline, to obtain a sheet-type medical polymer gel. The UV absorption spectrum of the resulting gel is shown in FIG. 3. The absorption peaks originated from Norfloxacin are observed at 280 nm and 330 nm.

EXAMPLE 12

According to the following method, it was prepared a medical polymer gel (see the formula below (VII)) comprising alginate gel as the water swelling polymer gel, —NH—$(CH_2)_2$—NH—CO—$CH_2$—NH—CO—$(CH_2)_2$—CO—as the spacer, -Ala-Ala-Phe- as the cleavable group and gentamycin (GM) as the drug.

roacetic acid salt ($(Lys)_2$-EDA.4TFA). The $(Lys)_2$-EDA.4TFA in total was dissolved in distilled water (50 ml), and passed through a column packed with diethylaminoethyl cellulose (DE52, Whatman; 20 g) equilibrated with an aqueous 1M HOSu solution. Then, the eluate was concentrated under reduced pressure, to obtain N,N'-di(L-lysyl)-ethylenediamine N-hydroxysuccinimide salt ($(Lys)_2$-EDA.4HOSu; 0.78 g). Yield; 40%.

$(Lys)_2$-EDA.4HOSu (0.29 g; 0.375 mmol) and EDC.HCl (0.96 g; 5 mmol) were dissolved in an aqueous 1 wt % solution (30 ml) of sodium alginate (500 to 600 cp; Wako Junyaku Industry, Kabushiki Kaisha), and the resulting solution was cast into a 12 cm×8 cm-polystyrene tray and was then left to stand at room temperature. About 15 hours later, a gel was obtained.

To the resulting gel after sufficient washing in water were added then Bos-Gly-EDA.HOSu (33 mg (0.1 mmol)) and EDC.HCl (0.38 g (2 mmol)) for overnight agitation at 4° C.

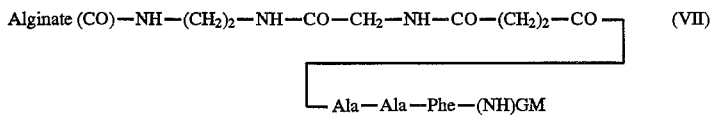

(VII)

$N^\alpha$-fluorenylmethoxycarbonyl-$N^\epsilon$-t-butyloxycarbonyl-L-lysine (Fmoc-Lys(Boc); 4.7 g (0.01 mol); Peptide Institute, Inc.) and HOSu (1.15 g (0.01 mol)) were dissolved in ethyl acetate (50 ml), followed by addition of DCC (1.7 g (0.011 mol)) under agitation in ice cooling, and subsequent agitation in ice cooling for another one hour and agitation overnight at room temperature. Filtering the insoluble matters off, the filtrate was concentrated under reduced pressure to deposit crystal, which was then recrystallized in isopropyl alcohol-ethyl acetate. The crystal was dried under reduced pressure to obtain $N^\alpha$-fluorenylmethoxycarbonyl-$N^\epsilon$-t-butyloxycarbonyl-L-lysyl-N-hydroxysuccinimide ester (Fmoc-Lys(Boc)-OSu) (4.7 g). Yield; 80%.

Fmoc-Lys(Boc)-OSu (2.82 g (5 mmol)) was dissolved in ethyl acetate (50 ml) and agitated at room temperature, followed by dropwise addition of a solution (10 ml) of ethylenediamine (0.15 g (2.5 mmol)) dissolved in ethyl acetate (50 ml). After completion of dropwise addition, agitation was further continued overnight. Filtering the deposit crystal and drying the crystal under reduced pressure, N,N'-($N^\alpha$-fluorenylmethoxycarbonyl-$N^\epsilon$-t-butyloxycarbonyl-L-lysyl)-ethylenediamine ((Fmoc-Lys(Boc))$_2$-EDA) was obtained. Yield; 100%.

The total amount of the obtained (Fmoc-Lys(Boc))$_2$-EDA was suspended in dioxane (200 ml), followed by addition of piperidine (40 ml; Wako Junyaku Industry, Kabushiki Kaisha) and agitation at room temperature for one hour. The crystal obtained via concentration under reduced pressure was washed in diethyl ether, to obtain N,N'-di($N^\epsilon$-t-butyloxycarbonyl-L-lysyl)-ethylenediamine ((Lys(Boc))$_2$-EDA). The obtained ((Lys(Boc))$_2$-EDA) in total was dissolved in trifluoroacetic acid (TFA; 10 ml), followed by agitation at room temperature for 2 hours. The crystal obtained via concentration under reduced pressure was washed in diethyl ether, followed by drying under reduced pressure to obtain N,N'-di(L-lysyl)-ethylenediamine trifluo- Furthermore, agitation was continued together with TFA (100 ml) in a polypropylene tray at room temperature for 2 hours. The amount of the introduced amino group was determined by the ninhydrin method, which was 0.34 μmol/ml.gel.

To the resulting gel was added succinic anhydride (20 mg; 0.1 mmol), followed by dropwise addition of an aqueous 5N NaOH solution under shaking to retain the pH around 7. About 5 hours later, the pH did not decrease any more. Almost no remaining amino group was detected in the gel after sufficient washing in pure water, but the amount of the carboxyl group introduced was calculated to be 0.34 μmol/ml.

To the gel were added HOSu (20 mg; 0.16 mmol) and EDC.HCl (160 mg; 0.8 mmol), followed by overnight agitation at 4° C. To the resulting solution was added -Ala-Ala-Phe- (13 mg; 40 μmol) synthesized by the solid phase synthesis and dissolved in PB (1 ml), followed by agitation overnight at 4° C. The resulting gel was sufficiently washed in water, followed by addition of HOSu (20 mg; 0.16 mmol) and EDC.HCl (160 mg; 0.8 mmol) for overnight agitation at 4° C. To the resulting solution were added GM (30 mg; 40 μmol) dissolved in an aqueous 0.05M NaHCO3 solution (20 ml) and EDC.HCl (38 mg; 0.2 mmol), for overnight agitation at 4° C. The resulting gel was sufficiently washed in physiological saline to obtain a transparent sheet-type medical polymer gel.

EXAMPLE 13

According to the following method, it was prepared a medical polymer gel (see the formula below (VIII)) comprising alginate gel as the water swelling polymer gel, —NH—$(CH_2)_2$—NH—CO—$CH_2$—NH—CO—$(CH_2)_2$—CO—as the spacer, -Gly-Pro-Leu-Gly-Pro- as the cleavable group and the transforming growth factor β (TGF β).

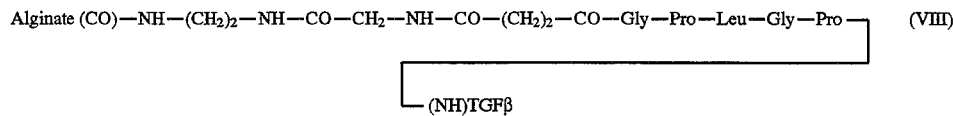

(VIII)

Into an aqueous 1 wt % solution (30 ml) of sodium alginate (at 500 to 600 cp; manufactured by Wako Junyaku industry, Kabushiki Kaisha) were dissolved Boc-Gly-EDA.HOSu (33 mg; 0.1 mmol) and (Lys)$_2$-EDA.4HOSu (0.29 g; 0.375 mmol) and EDC.HCl (0.96 g (5 mmol)), and the resulting solution was cast into a 12 cm×8 cm-polystyrene tray and was then left to stand at 4° C. for one day and subsequently to stand at room temperature for one day for gelling. In the same manner as in Example 12, TFA process was carried out. After sufficient washing, the introduced amino group of the gel in the state of water swelling was determined by the ninhydrin method, which was 30 μmol/ml. Furthermore, the reaction with succinic anhydride was done in the same manner as in Example 12, to introduce carboxyl groups. To the gel after sufficient washing were added HOSu (20 mg; 0.16 mmol) and EDC.HCl (160 mg; 0.8 mmol), for overnight agitation at 4° C. To the resulting solution was added Gly-Pro-Leu-Gly-Pro (22 mg; 50 μmol) synthesized by the solid phase synthesis and dissolved in PB (10 ml) followed by overnight agitation at 420 C. Furthermore, human TGF β (1 μg; Collaborative Inc.) dissolved in PB (10 ml) was added to the resulting solution, for overnight agitation at 4° C. The resulting gel was sufficiently washed in physiological saline, to obtain a transparent sheet-type medical polymer gel.

Comparative Example 5

According to the following method, it was prepared a medical polymer gel (see the formula below (IX)) comprising alginate gel as the water swelling polymer gel, -(Ala)$_2$-Pro-Val- as the cleavable group and Mafenide as the drug.

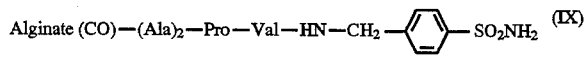

Alginate (CO)—(Ala)$_2$—Pro—Val—HN—CH$_2$—⟨  ⟩—SO$_2$NH$_2$  (IX)

In the same manner as in Example 8, (Ala)$_2$-Pro-Val-Mafenide (6 mg; 10 μmol) and EDC.HCl (96 mg; 0.5 mmol) were added to an aqueous 0.05M NaHCO$_3$ solution (5 ml) of 1 wt % sodium alginate, for overnight agitation at 4° C. Furthermore, Boc-Gly-EDA.HOSu (11 mg; 38 μmol) and EDC.HCl (0.19 g; 1 mmol) were added to and dissolved in the resulting mixture. The resulting solution was cast into a 3-cm petri dish, and was then left therein at room temperature for one day for gelling. The resulting gel was washed sufficiently in pure water for substitution with ethanol, followed by aseptic drying under reduced pressure, to obtain a medical polymer gel of a dry sheet type.

Comparative Example 6

According to the following method, it was prepared a medical polymer gel (see the formula below (X)) comprising PVA gel as the water swelling polymer gel, —CH$_2$—CH(OH)—CH$_2$—NH—CO—(CH$_2$)$_2$CO—as the spacer, and acrinol (ACR) as the drug.

Acrinol (361 mg; 1 mmol) and triethylamine (101 mg; 1 mmol) were dissolved in DMF (50 ml), followed by addition of succinic anhydride (300 mg; 3 mmol), and the resulting mixture was agitated overnight at room temperature. The resulting solution was precipitated thereafter in diethyl ether, followed by drying under reduced pressure to obtain Suc-ACR (250 mg). Yield; 70%.

The aminated PVA gel beads (100 mg) produced in Example 9 were suspended in an aqueous 0.05M NaHCO$_3$ solution (10 ml), followed by addition of Suc-ACR (4 mg; 10 μmol) and EDC.HCl (96 mg; 0.5 mmol) for overnight agitation at 4° C. After sufficient washing in water, substitution with ethanol was done followed by aseptic drying under reduced pressure, to obtain a medical polymer gel in beads.

Comparative Example 7

According to the following method, it was prepared a crystal cellulose powder immobilized with a drug (see the formula below (XI)) comprising crystal cellulose powder as the carrier, —CH$_2$—CH(OH)—CH$_2$—as the spacer, -Ala-Ala-Phe- as the cleavable group and gentamycin (GM) as the drug.

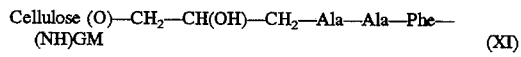

Cellulose (O)—CH$_2$—CH(OH)—CH$_2$—Ala—Ala—Phe—(NH)GM   (XI)

The crystal cellulose powder (CF-1, Whatman; 5 g) was dispersed in a mixture solution of an aqueous 1N NaOH solution (50 ml) and dioxane (50 ml), followed by addition of epichlorohydrin (10 ml) for agitation at 40° C. for 3 hours. After thorough washing, an aqueous 0.05M NaHCO$_3$ solution dissolving Ala-Ala-Phe (31 mg; 0.1 mmol) produced by a solid phase synthesis was added to the washed solution for overnight agitation at room temperature. After sufficient washing in water, substitution with dioxane was done followed by addition of HOSu (115 mg; 1 mmol) and DCC (210 mg; 1 mmol) for overnight agitation at room temperature. After sufficient washing in methanol, GM (75 mg; 0.1 mmol) dissolved in PB (10 ml) was added to the solution for overnight stirring at 4° C. After sufficient washing in physiological saline, crystal cellulose powder immobilized with the drug was obtained.

Test Example 3

Drug releasing test with elastase

The dry sheet produced in Example 8 or Comparative Example 5 (in the form of a disk of 3-cm diameter) was immersed in PBS (50 ml; 20 mM phosphate buffer, pH 7.4 containing 0.15M NaCl), and under occasional agitation at room temperature, aliquots of the supernatant were sampled after a given period. Additionally, elastase (pig pancreas, manufactured by Biozyme Lab. Ltd.) was added to the PBS solution to final concentrations of 10, 1, 0.1 U/ml. Then, aliquots of the supernatant were sampled after a given period of time. The amount of Mafenide in the samples was analyzed by HPLC. Prior to and after the addition of elastase, the amount of Mafenide in the supernatant was

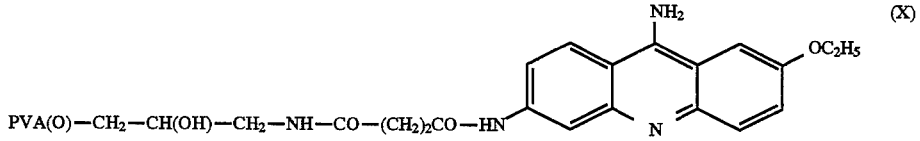

PVA(O)—CH$_2$—CH(OH)—CH$_2$—NH—CO—(CH$_2$)$_2$CO—HN⟨...⟩   (X)

determined. No release of Mafenide was observed in the dry sheet of Example 8 prior to the addition of elastase. However, rapid release of Mafenide was observed after the addition of elastase, depending on the elastase level. On the contrary, only the slight release of Mafenide was observed even after the addition of elastase in the dry sheet of Comparative Example 5.

Test Example 4

Drug releasing test with a *Pseudomonas aeruginosa* culture broth

*Pseudomonas aeruginosa* was cultured overnight in a dry bouillon medium (manufactured by Nissui Pharmaceutical Co., Ltd.) followed by centrifuge at 12,000 rpm for 15 minutes to obtain the supernatant. A 5-ml portion of the supernatant was incubated with the beads (100 mg) produced in Example 9 or Comparative Example 6 at room temperature for 2 hours. The level of acrinol released into the supernatant was determined on the basis of the absorbance at 410 nm. The amount of the released acrinol was 5 µmol from the beads of Example 9, while no release of acrinol was observed from the beads of Comparative Example 6.

Test Example 5

Drug releasing test with an enzyme solution

To a 0.5-g portion of each (in water swelling state) of the medical polymer gels of Examples 10 to 12 and the crystal cellulose powder immobilized with the drug of Comparative Example 7 were added 500 µl of 10 mM phosphate buffer containing 0.15M NACl (PBS, pH 7.4) and 1% trypsin (Difco 1:250) PBS solution (100 µl) for incubation at 37° C. for 3 hours. Thereafter, the supernatant was collected after centrifugation, which was designated test solution.

Test of formation of zones of growth inhibition of *Staphylococcus aureus*

*Staphylococcus aureus* overnight cultured in a Brain-Heart-Infusion medium (manufactured by Nissui Pharmaceutical Co., Ltd.) was uniformly inoculated at $5 \times 10^5$ cfu/plate on a Brain-Heart-Infusion agar medium plate (a diameter of 10 cm). A 8-mm diameter filter disk for assessing drug efficacy was preliminarily immersed in 75 µl of a test solution. The disk was placed on the plate inoculated with *Staphylococcus aureus*, followed by overnight culturing at 37° C. Due to the growth inhibition of *Staphylococcus aureus*, a zone was formed on the periphery of the filter disk immersed with the test solution. Then, the diameter of the zone was measured. The diameters via the test solutions of the medical polymer gels of Examples 10, 11 and 12, were 9 mm, 16 mm and 10 mm, respectively. In the crystal cellulose powder of Comparative Example 7 and in control groups of the medical polymer gels of Examples 10 to 12 with 100 µl PBS added therein instead of 100 µl of 1% trypsin-PBS solution, no zone of growth inhibition was observed.

Test Example 6

Together with a collagen sponge (Koken Kabushiki Kaisha), *Pseudonomas aeruginosa* ($10^7$ cfu) or *Staphylococcus aureus* ($10^9$ cfu) was inoculated on full thickness wounds (2 cm×2 cm) on back of the rat. The collagen sponges were removed and 24 hours later for *Pseudonomas aeruginosa* and 48 hours later for *Staphylococcus aureus*, respectively, and the wounds were washed by physiological saline. The wounds inoculated with *Pseudonomas aeruginosa* were attached with the medical polymer gel of Example 11; whereas the wounds inoculated with *Staphylococcus aureus* were attached with the medical polymer gel of Example 10. Twenty four hours later, the tissues were sampled from the wounds. Then, they were homogenized. A part of the homogenized tissues was serially diluted with PBS, and the resulting tissue solution was uniformly inoculated on a Brain-Heart-Infusion medium agar plate (a diameter of 10 cm). Based on the number of the colonies generated from overnight culture at 37° C., the number of bacteria in the tissue was calculated. The number of bacteria in the wounds attached with the medical polymer gel of Example 11 was $6.7 \times 10^4 \pm 8.9 \times 10^4$ cfu/g·tissues, whereas the number of bacteria in the tissue prior to the application was $1.1 \times 10^8 \pm 2.0 \times 10^7$ cfu/g·tissue. After comparison, apparent decrease in the number of bacteria was observed. The number of bacteria in the wounds attached with the medical polymer gel of Example 10 was $1.2 \times 10^6 \pm 1.1 \times 10^6$ cfu/g·tissues, whereas the number of bacteria in the tissue prior to the application was $2.2 \times 10^7 \pm 4.9 \times 10^6$ cfu/g·tissue. After comparison, apparent decrease in the number of bacteria was observed.

The Test Examples indicate that the medical polymer gel of the present invention exerts a drug releasing property corresponding to the amount of the enzyme present, apparently showing the effect of decreasing the number of bacteria in wounds with bacterial infection in animals.

The abbreviations of individual amino acid residues used in the specification are shown as follows:

Ala: L-alanine residue
Arg: L-arginine residue
Asn: L-asparagine residue
Asp: L-aspartic acid residue
Cys: L-cysteine residue
Gln: L-glutamine residue
Glu: L-glutamic acid residue
Gly: glycine residue
His: L-hystidine residue
Ile: L-isoleucine residue
Leu: L-leucine residue
Lys: L-lysine residue
Phe: L-phenylalanine residue
Pro: L-proline residue
Ser: L-serine residue
Thr: L-threonine residue
Trp: L-tryptophan residue
Tyr: L-tyrosine residue
Val: L-valine residue
Nle: L-norleucine residue In the present specification, the amino acid sequence of a peptide is depicted according to the common method; the amino acid residue at N-terminal is positioned at the left side while the amino acid residue at C-terminal is positioned at the right side. Amino acids of D-configuration are shown as its abbreviation followed by the symbol (D).

INDUSTRIAL APPLICABILITY

Because the medical polymer gel of the present invention exerts a drug releasing property depending on the level of an enzyme, the gel can release a therapeutically effective amount of a drug only at a focal lesion generating the enzyme. The medical polymer gel of the present invention is useful as the structural component of wound dressings, adhesives for biological tissues, adhesion preventing agents, bone reinforcing agents, and drug releasing materials. For treatment of inflammation and healing and promotion thereof, the gel can be applied to sites of wounds including general wounds such as scar and cut; artificial dermal defects such as dermatome wounds and dermabrasion wounds; surgery wounds such as cut; burn; ulcer and decubitus. Furthermore, the gel can be applied also to adhesion of wounds after surgery, prevention of adhesion of wounds to other tissues after surgery, bone reinforcement for osteoporosis and bone fracture, and treatment of malignant neoplasm.

Wound dressings comprising the structural material of the water swelling polymer gel (II) provided by the present invention, can be applied to a patient with wounds such as cut, burn, and decubitus to treat and promote the healing of the wounds of the patient. During the application, the state of the wounds can be observed without detaching the dressings, so that the dressings are very useful for the control of the wounds, whereby the number of dressing exchange can be decreased.

TABLE 1

| | Form | Handling | Flexibility | Thermal resistance (at 121° C. for 20 min.) | Compression performance (initial stress/ distortion, breaking strength) | Transparency (transmittance at 400 nm) | Water absorption ratio (fluid similar to intercellular fluid) | Solubility (in water) | Durability (in PBS at 37° C. under agitation for 24 hours) | Cyto- toxicity (L929 cell) |
|---|---|---|---|---|---|---|---|---|---|---|
| Example 1 | Sheet- type gel | Excellent (held with forceps) | Excellent | Excellent | Viscous elastic body (12 g/mm, 220 g) | Excellent (89%) | 93 | Insoluble | Excellent | No |
| Comparative Example 2 | Sheet- type gel | Excellent (held with forceps) | Excellent | Excellent | Elastic body (40 g/mm, 60 g) | Excellent (79%) | 108 | Partially soluble | Poor (decomposed in pieces) | No |
| Comparative Example 3 | Sheet- type gel | Poor (never held with forceps) | Excellent | Excellent | Viscous elastic body (4.5 g/mm, 50 g) | Excellent (99%) | 245 | Partially soluble | Excellent | No |
| Comparative Example 4 | Film- type | Excellent (held with forceps) | Poor (broken during bending) | Excellent | Elastic body (570 g/mm, 700 g) | Poor (31%) | 3.2 | Insoluble | Poor (decomposed in pieces) | No |

What is claimed is:

1. A water swelling polymer gel produced by covalently crosslinking a polysaccharide having a carboxyl group within the molecule with a crosslinking reagent represented by the following general formula (II):

$$R^1HN-(CH_2)_n-NHR^2 \quad (II)$$

(wherein n represents an integer of 2 to 18; and $R^1$ and $R^2$ independently represent hydrogen atom or the group represented by $-COCH(NH_2)-(CH_2)_4-NH_2$) or a salt thereof, in which the crosslinking reagent is present in an amount of 1 to 50 mole % with respect to the carboxyl group of the polysaccharide.

2. A water swelling polymer gel according to claim 1, wherein the polysaccharide having a carboxyl group within the molecule is a salt of alginic acid or a salt of hyaluronic acid.

3. A water swelling polymer gel according the claim 2, wherein the salt of the crosslinking reagent is the N-hydroxysuccinimide salt.

4. A water swelling polymer gel according to claim 1, wherein the salt of the crosslinking reagent is the N-hydroxysuccinimide salt.

5. A water swelling polymer gel according to claim 4, wherein the N-hydroxysuccinimide salt of the crosslinking agent is selected from the group consisting of 2N-hydroxysuccinimide salt of diaminoethane, 2N-hydroxysuccinimide salt of diaminohexane, 4N-hydroxysuccinimide salt of N,N'-di(lysyl)- diaminoethane, and 3N-hydroxysuccinimide salt of N-(lysyl)-diaminohexane.

* * * * *